United States Patent
Stahmann et al.

(10) Patent No.: US 11,903,589 B2
(45) Date of Patent: Feb. 20, 2024

(54) MEDICAL SYSTEM FOR TREATING A LEFT ATRIAL APPENDAGE

(71) Applicant: BOSTON SCIENTIFIC SCIMED, INC., Maple Grove, MN (US)

(72) Inventors: Jeffrey E. Stahmann, Ramsey, MN (US); Bin Mi, Arden Hills, MN (US); Eric Wedul, Farmington, MN (US); Keith R. Maile, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 219 days.

(21) Appl. No.: 17/209,938

(22) Filed: Mar. 23, 2021

(65) Prior Publication Data

US 2021/0298763 A1    Sep. 30, 2021

Related U.S. Application Data

(60) Provisional application No. 62/993,796, filed on Mar. 24, 2020.

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12131* (2013.01);
(Continued)

(58) Field of Classification Search
CPC ........ A61B 17/12122; A61B 17/12031; A61B 17/12131; A61B 2017/00221;
(Continued)

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| CN | 1399571 A | 2/2003 |
| CN | 202143640 U | 2/2012 |

(Continued)

OTHER PUBLICATIONS

International Search Report and Written Opinion dated Oct. 13, 2020 for International Application No. PCT/US2020/048437.
(Continued)

*Primary Examiner* — Tan-Uyen T Ho
*Assistant Examiner* — David P Stein
(74) *Attorney, Agent, or Firm* — Seager, Tufte & Wickhem LLP

(57) ABSTRACT

A medical system may include a left atrial appendage closure device including an expandable framework and a proximal hub centered on a central longitudinal axis of the framework. An insert may be disposed within the proximal hub and include a collar configured to engage the proximal hub, a recess extending into the insert from a proximal end, and a post member disposed within the recess. The post member may be radially spaced apart from the collar and may extend proximally from a distal end of the recess to a proximal surface. The insert may include a first connection structure disposed distal of the proximal surface. The medical system may include a delivery catheter having a second connection structure configured to engage the first connection structure in a delivery configuration. The distal end of the delivery catheter includes a hollow portion configured to receive the post member in the delivery configuration.

19 Claims, 17 Drawing Sheets

(52) U.S. Cl.
CPC .............. *A61B 2017/00221* (2013.01); *A61B 2017/12095* (2013.01); *A61B 2562/0214* (2013.01); *A61B 2562/0247* (2013.01)

(58) Field of Classification Search
CPC .. A61B 2017/12095; A61B 2562/0214; A61B 2562/0247; A61B 17/12177; A61B 2017/00734; A61B 2017/12054; A61B 2090/064; A61B 17/12172
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ue |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |

(56) References Cited

U.S. PATENT DOCUMENTS

| | | |
|---|---|---|
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muij Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |

(56) References Cited

U.S. PATENT DOCUMENTS

| | | |
|---|---|---|
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,137,953 B2 | 11/2006 | Eigler et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,317,951 B2 | 1/2008 | Schneider et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,100,938 B2 | 1/2012 | Figulla et al. |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,728,117 B1 | 5/2014 | Janardhan et al. |
| 8,758,389 B2 | 6/2014 | Glimsdale |
| 8,828,051 B2 | 9/2014 | Javois et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,211,124 B2 | 12/2015 | Campbell et al. |
| 9,295,472 B2 | 3/2016 | Ottma |
| 9,351,716 B2 | 5/2016 | Miles et al. |
| 9,445,895 B2 | 9/2016 | Kreidler |
| 9,554,804 B2 | 1/2017 | Erzbeger |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,592,058 B2 | 3/2017 | Erzbeger et al. |
| 9,597,088 B2 | 3/2017 | Ottma |
| 9,629,636 B2 | 4/2017 | Fogarty et al. |
| 9,730,701 B2 | 8/2017 | Tischler et al. |
| 9,743,932 B2 | 8/2017 | Amplatz et al. |
| 9,750,505 B2 | 9/2017 | Miles et al. |
| 9,763,666 B2 | 9/2017 | Wu et al. |
| 9,795,387 B2 | 10/2017 | Miles et al. |
| 9,808,253 B2 | 11/2017 | Li et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 10,201,337 B2 | 2/2019 | Glimsdale |
| 10,231,737 B2 | 3/2019 | Amplatz et al. |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |

(56) References Cited

U.S. PATENT DOCUMENTS

| | | |
|---|---|---|
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0212432 A1 | 11/2003 | Khairkhahan et al. |
| 2003/0220667 A1 | 11/2003 | van der Burg et al. |
| 2004/0034366 A1 | 2/2004 | van der Burg et al. |
| 2004/0044361 A1 | 3/2004 | Frazier et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004641 A1 | 1/2005 | Pappu |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2006/0247680 A1 | 11/2006 | Amplatz et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0112380 A1 | 5/2007 | Figulla et al. |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0271337 A1 | 10/2012 | Figulla et al. |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0131717 A1 | 5/2013 | Glimsdale |
| 2013/0165735 A1 | 6/2013 | Khairkhahan et al. |
| 2013/0211492 A1 | 8/2013 | Schneider et al. |
| 2013/0296912 A1 | 11/2013 | Ottma |
| 2013/0331884 A1 | 12/2013 | Van der Burg et al. |
| 2013/0338686 A1 | 12/2013 | Ruiz |
| 2014/0005714 A1 | 1/2014 | Quick et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0214077 A1 | 7/2014 | Glimsdale |
| 2014/0296908 A1 | 10/2014 | Ottma et al. |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2014/0364941 A1 | 12/2014 | Edmiston et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0015397 A1 | 1/2016 | Figulla et al. |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0007262 A1 | 1/2017 | Amplatz et al. |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0119400 A1 | 5/2017 | Amplatz et al. |
| 2017/0181751 A1 | 6/2017 | Larsen et al. |
| 2017/0340336 A1 | 11/2017 | Osypka |
| 2017/0354421 A1 | 12/2017 | Maguire et al. |
| 2018/0064446 A1 | 3/2018 | Figulla et al. |
| 2018/0070950 A1 | 3/2018 | Zaver et al. |
| 2018/0110468 A1* | 4/2018 | Goldshtein ........ A61B 17/0057 |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2018/0369594 A1 | 12/2018 | Werneth et al. |
| 2019/0133563 A1 | 5/2019 | Glimsdale |
| 2019/0175185 A1 | 6/2019 | Amplatz et al. |
| 2019/0223883 A1 | 7/2019 | Anderson et al. |
| 2019/0247053 A1 | 8/2019 | Inouye |
| 2019/0336135 A1 | 11/2019 | Inouye et al. |
| 2020/0229957 A1* | 7/2020 | Bardsley .......... A61B 17/12113 |
| 2021/0228216 A1* | 7/2021 | Brinkmann ...... A61B 17/12177 |

FOREIGN PATENT DOCUMENTS

| | | |
|---|---|---|
| CN | 104352261 A | 2/2015 |
| CN | 106859722 A | 6/2017 |
| CN | 10964173 A | 3/2019 |
| DE | 10201004476 A1 | 3/2012 |
| EP | 1523957 A2 | 4/2005 |
| EP | 1595504 A1 | 11/2005 |
| EP | 2074953 A1 | 1/2009 |

(56) References Cited

FOREIGN PATENT DOCUMENTS

| | | | |
|---|---|---|---|
| EP | 2481381 A1 | 8/2012 | |
| EP | 2928420 A1 | 10/2015 | |
| EP | 3072461 A1 | 9/2016 | |
| EP | 3372173 A2 | 9/2018 | |
| EP | 3398523 A1 | 11/2018 | |
| IN | 104287804 A | 1/2015 | |
| JP | 2003532457 A | 11/2003 | |
| JP | 2005324019 A | 11/2005 | |
| JP | 2007513684 A | 5/2007 | |
| JP | 2009160402 A | 7/2009 | |
| JP | 2012501793 A | 1/2012 | |
| WO | 9313712 A1 | 7/1993 | |
| WO | 9504132 A1 | 2/1995 | |
| WO | 9522359 A1 | 8/1995 | |
| WO | 9601591 A1 | 1/1996 | |
| WO | 9640356 A1 | 12/1996 | |
| WO | 9721402 A1 | 6/1997 | |
| WO | 9726939 A1 | 7/1997 | |
| WO | 9728749 A1 | 8/1997 | |
| WO | 9735522 A1 | 10/1997 | |
| WO | 9802100 A1 | 1/1998 | |
| WO | 9817187 A1 | 4/1998 | |
| WO | 9822026 A1 | 5/1998 | |
| WO | 9823322 A1 | 6/1998 | |
| WO | 9827868 A1 | 7/1998 | |
| WO | 9905977 A1 | 2/1999 | |
| WO | 9907289 A1 | 2/1999 | |
| WO | 9908607 A1 | 2/1999 | |
| WO | 9923976 A1 | 5/1999 | |
| WO | 9925252 A1 | 5/1999 | |
| WO | 9930640 A1 | 6/1999 | |
| WO | 9944510 A1 | 9/1999 | |
| WO | 9959479 A1 | 11/1999 | |
| WO | 0001308 A1 | 1/2000 | |
| WO | 0016705 A1 | 3/2000 | |
| WO | 0027292 A1 | 5/2000 | |
| WO | 0035352 A1 | 6/2000 | |
| WO | 0053120 A1 | 9/2000 | |
| WO | 0067669 A1 | 11/2000 | |
| WO | 0108743 A1 | 2/2001 | |
| WO | 0115629 A1 | 3/2001 | |
| WO | 0121247 A1 | 3/2001 | |
| WO | 0126726 A1 | 4/2001 | |
| WO | 0130266 A1 | 5/2001 | |
| WO | 0130267 A1 | 5/2001 | |
| WO | 0130268 A1 | 5/2001 | |
| WO | 0170119 A1 | 9/2001 | |
| WO | 0215793 A2 | 2/2002 | |
| WO | 0224106 A2 | 3/2002 | |
| WO | 02071977 A2 | 9/2002 | |
| WO | 03007825 A1 | 1/2003 | |
| WO | 03008030 A2 | 1/2003 | |
| WO | 03032818 A1 | 4/2003 | |
| WO | 2004012629 A1 | 2/2004 | |
| WO | 2007044536 A1 | 4/2007 | |
| WO | 2010024801 A1 | 3/2010 | |
| WO | 2010081033 A1 | 7/2010 | |
| WO | 2013060855 A1 | 5/2013 | |
| WO | 2013159065 A1 | 10/2013 | |
| WO | 2014011865 A1 | 1/2014 | |
| WO | 2014018907 A1 | 1/2014 | |
| WO | 2014089129 A1 | 6/2014 | |
| WO | 201406239 A1 | 7/2014 | |
| WO | 2015164836 A1 | 10/2015 | |
| WO | 2016087145 A1 | 6/2016 | |
| WO | 2018017935 A1 | 1/2018 | |
| WO | 2018187732 A1 | 10/2018 | |
| WO | 2019084358 A1 | 5/2019 | |

OTHER PUBLICATIONS

International Search Report and Written Opinion dated Jul. 15, 2021 for International Application No. PCT/US2021/023687.
International Search Report and Written Opinion dated Aug. 3, 2004 for International Application No. PCT/US2004/008109.
International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al., "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation, Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation To Pay Additional Fees And, Where Applicable, Protest Fee, dated Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 2020, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.

(56) References Cited

OTHER PUBLICATIONS

International Search Report and Written Opinion dated Oct. 23, 2020 for International Application No. PCT/US2020/042192.

* cited by examiner

MEDICAL SYSTEM FOR TREATING A LEFT ATRIAL APPENDAGE

CROSS-REFERENCE TO RELATED APPLICATIONS

This application claims the benefit of priority of U.S. Provisional Application No. 62/993,796 filed Mar. 24, 2020, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices and introducers as well as alternative methods for manufacturing and using medical devices and introducers.

SUMMARY

In a first aspect, a medical system may comprise a left atrial appendage closure device including an expandable framework and a proximal hub centered on a central longitudinal axis of the expandable framework. An insert may be disposed within the proximal hub, the insert including a collar configured to engage the proximal hub, a recess extending into the insert from a proximal end of the insert, and a post member disposed within the recess. The post member may be radially spaced apart from the collar to define a gap between the post member and the collar, and the post member may extend proximally from a distal end of the recess to a proximal surface. The insert may include a first connection structure disposed distal of the proximal surface. The medical system may comprise a delivery catheter having a second connection structure proximate a distal end of the delivery catheter, the second connection structure being configured to engage the first connection structure in a delivery configuration of the medical system. The distal end of the delivery catheter includes a hollow portion configured to receive the post member in the delivery configuration.

In addition or alternatively to any aspect described herein, a sensor is disposed within the post member.

In addition or alternatively to any aspect described herein, the sensor is a pressure sensor and the proximal surface is a diaphragm extending across a proximal end of the post member, the diaphragm being configured to transmit a pressure within a left atrium to the pressure sensor when the expandable framework is disposed within an ostium of the left atrial appendage.

In addition or alternatively to any aspect described herein, the delivery catheter includes at least one aperture extending through a side wall of the delivery catheter proximate the distal end of the delivery catheter.

In addition or alternatively to any aspect described herein, the left atrial appendage closure device includes a gap seal configured to extend across a proximal end of the gap when the medical system is disposed in a released configuration in which the delivery catheter is disengaged from the left atrial appendage closure device.

In addition or alternatively to any aspect described herein, the gap seal is configured to deflect into the recess when the medical system is in the delivery configuration.

In addition or alternatively to any aspect described herein, the first connection structure includes a first threaded portion disposed on an outside surface of the post member or an inside surface of the collar.

In addition or alternatively to any aspect described herein, the second connection structure includes a second threaded portion disposed proximate the distal end of the delivery catheter, the second threaded portion being configured to threadably mate with the first threaded portion when the medical system is in the delivery configuration.

In addition or alternatively to any aspect described herein, the first connection structure includes at least one groove formed in an outside surface of the post member or to an inside surface of the collar, wherein the at least one groove includes a longitudinal portion and a circumferential portion extending from a distal end of the longitudinal portion.

In addition or alternatively to any aspect described herein, the second connection structure includes at least one radially extending projection proximate the distal end of the delivery catheter, the at least one radially extending projection being configured to engage the at least one groove when the medical system is in the delivery configuration.

In addition or alternatively to any aspect described herein, the first connection structure includes at least one projection extending radially outward from the post member.

In addition or alternatively to any aspect described herein, the second connection structure includes two or more movable jaws configured to engage the at least one projection to clamp the post member between the two or more movable jaws when the medical system is in the delivery configuration.

In addition or alternatively to any aspect described herein, the first connection structure includes a channel formed in an outside surface of the post member and extending circumferentially around the post member distal of the proximal surface.

In addition or alternatively to any aspect described herein, the second connection structure includes: a distal cap member disposed at the distal end of the delivery catheter and configured to span the proximal surface of the post member, wherein the distal cap member includes at least one aperture formed in a laterally extending surface of the distal cap member; and a tether extending longitudinally alongside the delivery catheter, through the at least one aperture, and around the post member within the channel when the medical system is in the delivery configuration.

In addition or alternatively to any aspect described herein, a medical system may comprise a left atrial appendage closure device including an expandable framework and a proximal hub centered on a central longitudinal axis of the expandable framework. An insert may be disposed within the proximal hub, the insert including a collar defining a circumferential wall of the insert configured to engage the proximal hub, a recess extending axially into the insert from a proximal end of the insert, and a post member disposed within the recess. The post member may be radially spaced apart from the collar to define an annular gap between the post member and the collar, and the post member may extend proximally from a distal end of the recess to a proximal surface disposed proximate the proximal end of the insert. The insert may include a first connection structure disposed distal of the proximal surface. A pressure sensor may be disposed within the post member and in communication with the proximal surface of the post member for sensing a fluid pressure proximal of the left atrial appendage closure device. The medical system may comprise a delivery catheter having a second connection structure proximate a distal end of the delivery catheter, the second connection structure being configured to engage the first connection structure in a delivery configuration of the medical system. The distal end of the delivery catheter may include a hollow portion configured to extend over the post member and within the circumferential wall in the delivery configuration such that the distal end of the delivery catheter is disposed distal of the proximal end of the insert.

In addition or alternatively to any aspect described herein, a medical system may comprise a left atrial appendage closure device including a self-expanding framework and a proximal hub centered on a central longitudinal axis of the expandable framework. An insert may be disposed within the proximal hub, the insert including a collar defining a circumferential wall of the insert configured to engage the proximal hub, a recess extending axially into the insert from a proximal end of the insert, and a post member disposed within the recess radially inward of the circumferential wall. The post member may extend proximally from a distal end of the recess to a proximal surface. A sensor, a capacitor, and a communication coil may be disposed within the insert. The medical system may comprise a delivery catheter including a hollow portion disposable within the insert radially inward of the circumferential wall and radially outward of the post member in a delivery configuration of the medical system.

In addition or alternatively to any aspect described herein, the insert includes a first connection structure disposed distal of the proximal surface of the post member and the delivery catheter includes a second connection structure configured to engage the first connection structure in the delivery configuration of the medical system.

In addition or alternatively to any aspect described herein, in the delivery configuration of the medical system, the delivery catheter does not contact the proximal surface of the post member.

In addition or alternatively to any aspect described herein, the left atrial appendage closure device includes an occlusive element disposed over at least a portion of the expandable framework. The expandable framework is configured to shift between a collapsed configuration and a deployed configuration. The occlusive element is configured to prevent thrombi from exiting a left atrial appendage when the expandable framework is disposed within an ostium of the left atrial appendage in the deployed configuration.

In addition or alternatively to any aspect described herein, the expandable framework includes a plurality of interconnected struts joined together at the proximal hub.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
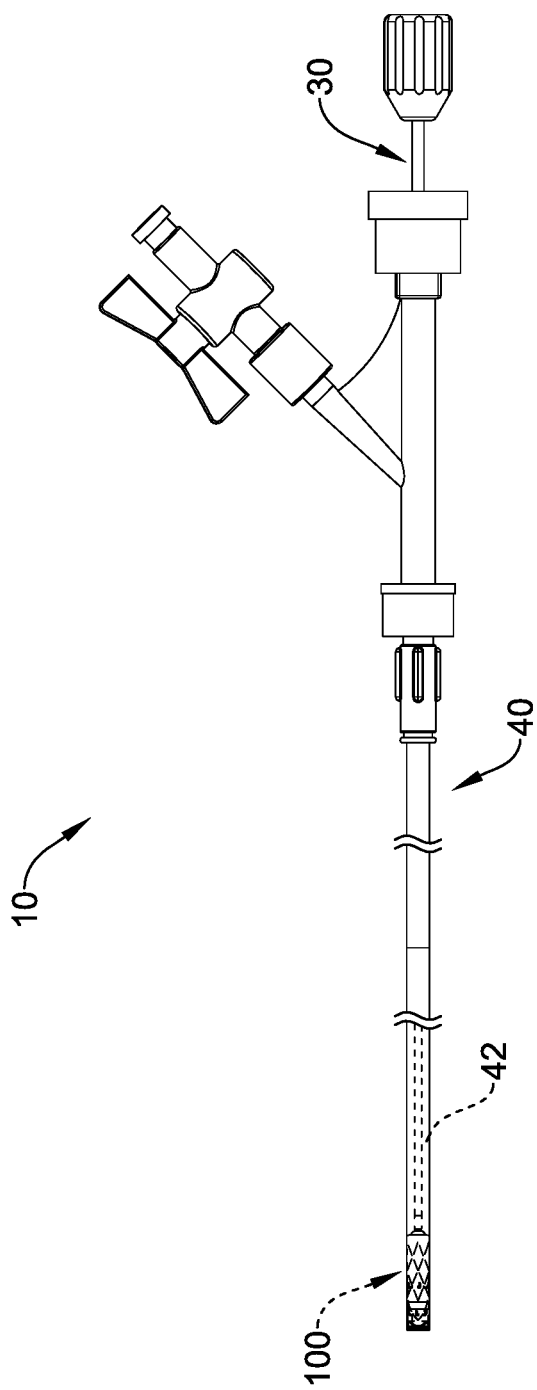
FIGS. 1-2 are side views of an example medical system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a medical system for occluding the left atrial appendage, and/or methods of using the implant and/or the medical system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

Figure 2:
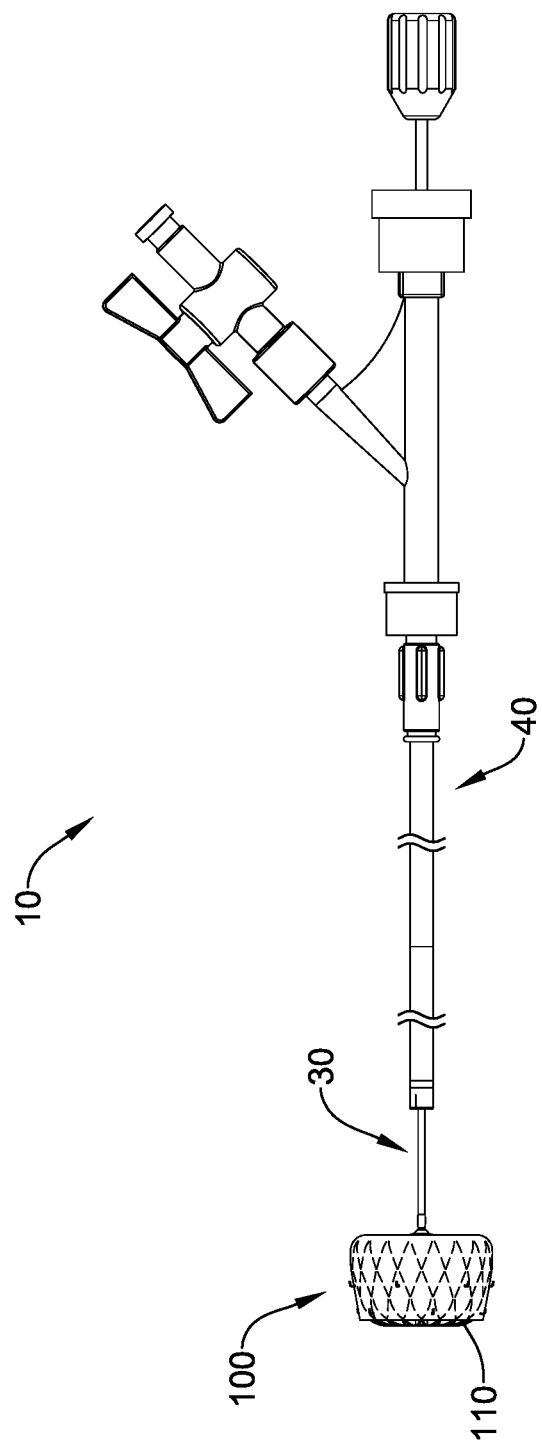

Turning now to the figures, FIGS. 1-2 illustrate a medical system 10 including an outer sheath 40 having a lumen 42 extending from a proximal opening to a distal opening, a delivery catheter 30 slidably disposed within the lumen 42, and a left atrial appendage closure device 100 having an expandable framework 110 configured to shift between a collapsed configuration (e.g., FIG. 1), wherein the left atrial appendage closure device 100 is disposed within the lumen 42 proximate the distal opening in the collapsed configuration, and a deployed configuration (e.g., FIG. 2). The left atrial appendage closure device 100 and/or the expandable framework 110 may be configured to shift between the collapsed configuration and the deployed configuration when the left atrial appendage closure device 100 is disposed distal of the distal opening of the lumen 42 and/or the outer sheath 40, and/or when the left atrial appendage closure device 100 is unconstrained by the outer sheath 40. The left atrial appendage closure device 100 may be disposed at and/or releasably connected to a distal portion of the delivery catheter 30. The delivery catheter 30 may be slidably and/or rotatably disposed within the lumen 42 of the outer sheath 40. In some embodiments, a proximal end of the delivery catheter 30 may extend proximally of a proximal end of the outer sheath 40 and/or the proximal opening of the lumen 42 for manual manipulation by a clinician or practitioner. In some embodiments, the example left atrial appendage closure device 100 may be removably attached, joined, or otherwise connected to the distal end of the delivery catheter 30. Some suitable, but non-limiting, examples of materials for the medical system 10, the delivery catheter 30, the outer sheath 40, and/or the left atrial appendage closure device 100, etc. are discussed below. It is contemplated that any and/or all example occlusive implants disclosed herein may be used in accordance with and/or be associated with the example medical system 10 described above.

Figure 3:
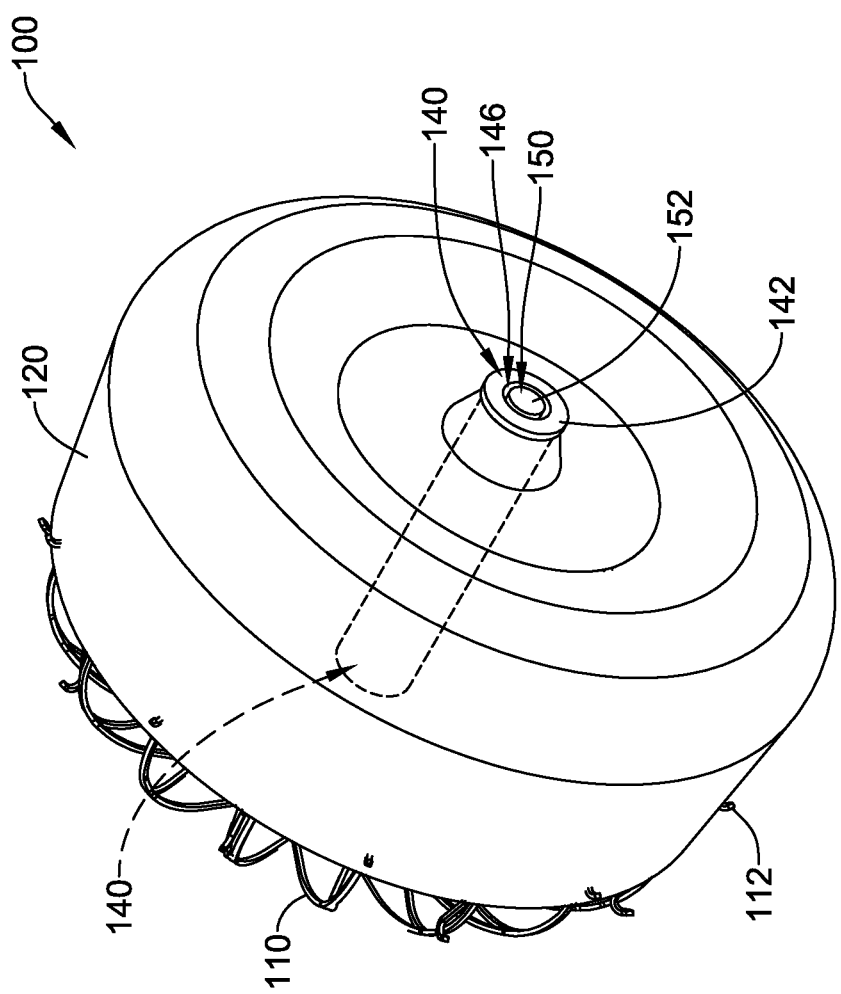
FIGS. 3-4 illustrate aspects of a left atrial appendage closure device.
Figure 4:
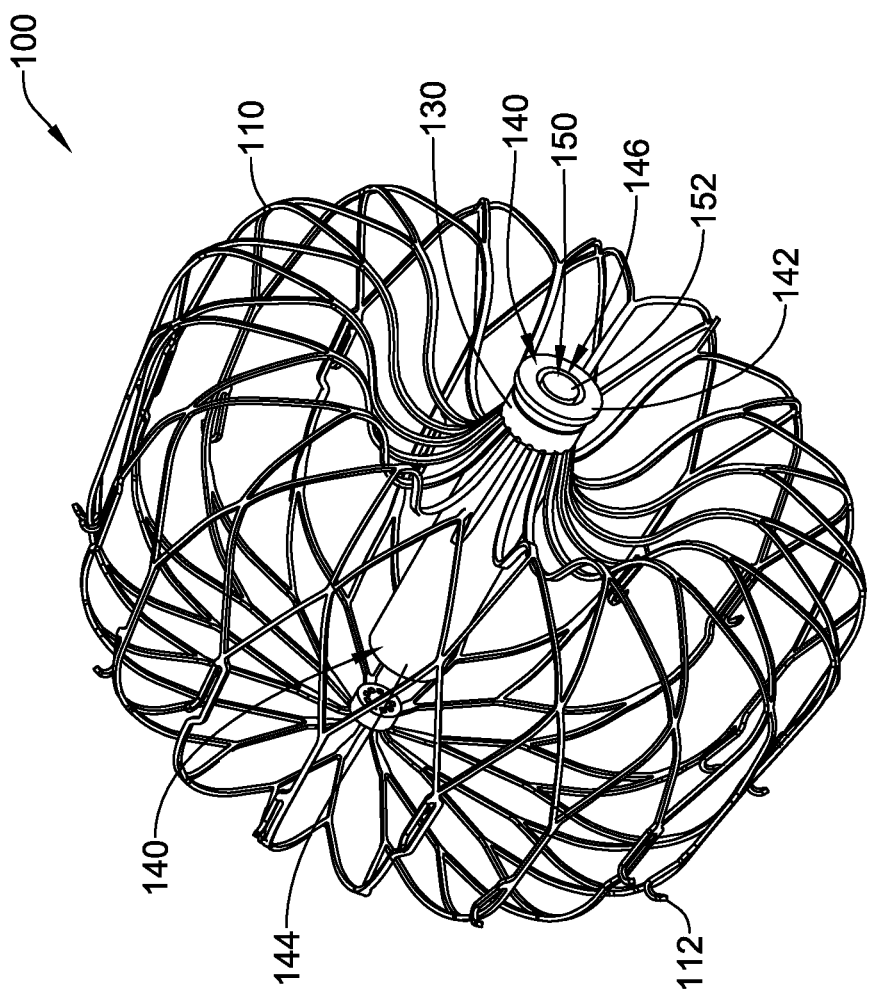

FIGS. 3-4 illustrate an example configuration of the left atrial appendage closure device 100 comprising the expandable framework 110 configured to shift between the collapsed configuration and the expanded configuration. In some embodiments, the left atrial appendage closure device 100 may include a proximal hub 130 centered on a central longitudinal axis of the expandable framework 110. For example, the proximal hub 130 may be coaxial with the central longitudinal axis of the expandable framework 110. In some embodiments, the expandable framework 110 may include a plurality of interconnected struts joined together at the proximal hub 130. In some embodiments, the proximal hub 130 may be integrally formed with and/or may be monolithically formed with the expandable framework 110 and/or the plurality of interconnected struts. In some embodiments, the left atrial appendage closure device 100 may include, and/or the expandable framework 110 may be, a self-expanding framework.

The expandable framework 110 may be compliant and substantially conform to and/or be in sealing engagement with the shape and/or geometry of a lateral wall and/or an ostium of a left atrial appendage in the expanded configuration. In some embodiments, the left atrial appendage closure device 100 may expand to a size, extent, or shape less than or different from a maximum unconstrained extent, as determined by the surrounding tissue and/or lateral wall of the left atrial appendage. Reducing a thickness of various elements of the expandable framework 110 may increase the flexibility and compliance of the expandable framework 110 and/or the left atrial appendage closure device 100, thereby permitting the expandable framework 110 and/or the left atrial appendage closure device 100 to conform to the tissue around it, rather than forcing the tissue to conform to the expandable framework 110 and/or the left atrial appendage closure device 100.

In some embodiments, the left atrial appendage closure device 100 may optionally include an occlusive element 120 (e.g., a mesh, a fabric, a membrane, and/or other surface treatment) disposed on, disposed over, disposed about, or covering at least a portion of the expandable framework 110, as seen in FIG. 3. In some embodiments, the occlusive element 120 may be disposed on, disposed over, disposed about or cover at least a portion of an outer (or outwardly facing) surface of the expandable framework 110. In some embodiments, the occlusive element 120 may be secured to and/or may extend radially outward from the proximal hub 130.

In some embodiments, the expandable framework 110 may include a plurality of anchor members 112 disposed about a periphery of the expandable framework 110 in the expanded configuration. The plurality of anchor members 112 may extend radially outward from the expandable framework 110. In some embodiments, at least some of the plurality of anchor members 112 may each have and/or include a body portion, a tip portion, and a barb projecting circumferentially therefrom. In some embodiments, some and/or each of the plurality of anchor members 112 have at least one barb projecting circumferentially therefrom. Some suitable, but non-limiting, examples of materials for the expandable framework 110, the plurality of anchor members 112, etc. are discussed below.

In some embodiments, the plurality of anchor members 112 may provide an anchoring mechanism to aid in retaining the left atrial appendage closure device 100 at a target site within a patient's anatomy (i.e., the left atrial appendage, for example) in the expanded configuration. However, the barb(s) may be configured, positioned, and/or arranged such that engagement of the barb(s) with surrounding tissue at the target site is minimized or avoided. For example, the barb(s) may not puncture, pierce, and/or extend into the surrounding tissue in the expanded configuration. Additionally, in some embodiments, the plurality of anchor members 112 may provide an attachment mechanism for securing the occlusive element 120 to the expandable framework 110.

In some embodiments, the occlusive element 120 may extend distally past at least some of the plurality of anchor members 112. In some embodiments, the occlusive element 120 may extend distally past each and/or all of the plurality of anchor members 112. In at least some embodiments, at least a distal portion of the occlusive element 120 may be attached to the expandable framework 110. In some embodiments, at least some of the plurality of anchor members 112 extend and/or project through the occlusive element 120. In some embodiments, each and/or all of the plurality of anchor members 112 extend and/or project through the occlusive element 120. In some embodiments, the membrane or occlusive element may be attached to the frame at some and/or each of the plurality of anchor members 112, for example, by passing some and/or each of the plurality of anchor members 112 through the occlusive element 120.

In some embodiments, the barb and/or the tip portion on some and/or each of the at least some of the plurality of anchor members 112 may be disposed radially outward of the occlusive element 120 and/or exterior of the occlusive element 120 while the base of its respective anchor member is disposed radially inward of and/or interior of the occlusive element 120. The barb may serve to retain the occlusive element 120 on the expandable framework 110, thereby preventing the occlusive element 120 from working loose and/or releasing from the expandable framework 110 as the expandable framework 110 is shifted between the collapsed configuration and the deployed configuration. In some embodiments, attachment of the distal portion of the occlusive element 120 to the expandable framework 110 is devoid of sutures and/or adhesives.

In one example, when the left atrial appendage closure device 100 and/or the expandable framework 110 is shifted to the collapsed configuration for delivery and/or disposal within the lumen 42 of the outer sheath 40, the occlusive element 120 may be placed in tension and/or stretched tight along the outer surface of the expandable framework 110 and/or result in a portion of the expandable framework 110 deforming and/or buckling under the tension of the occlusive element 120. The tension may be reduced by extending and/or increasing the length of the occlusive element 120 while keeping and/or maintaining the length of the expandable framework 110. To accommodate the changes in tension, the occlusive element 120 may be free to move axially along the body portion of the at least some of the plurality of anchor members 112 extending through the occlusive element 120. For example, the occlusive element 120 may be devoid of fixed attachment (e.g., may not be fixedly secured in place, such as with sutures or adhesives) to the plurality of anchor members 112 and/or the expandable framework 110. The barb(s) may prevent the occlusive element 120 from slipping off the at least some of the plurality of anchor members 112 extending through the occlusive element 120 when the left atrial appendage closure device 100 and/or the expandable framework 110 is shifted to the deployed configuration and the tension is released or reduced.

In some embodiments, the occlusive element 120 may be permeable, semi-permeable, or impermeable to blood and/or other fluids, such as water. In some embodiments, the occlusive element 120 may include a polymeric membrane, a metallic or polymeric mesh, a porous filter-like material, or other suitable construction. In some embodiments, the occlusive element 120 may be configured to prevent thrombi (i.e. blood clots, etc.) from passing through the occlusive element 120 and/or exiting the left atrial appendage into the blood stream when the left atrial appendage closure device 100 and/or the expandable framework 110 is disposed within an ostium of the left atrial appendage in the deployed configuration. In some embodiments, the occlusive element 120 may be configured to promote endothelization across the ostium of the left atrial appendage after implantation of the left atrial appendage closure device 100, thereby effectively removing the left atrial appendage from the patient's circulatory system. Some suitable, but non-limiting, examples of materials for the occlusive element 120 are discussed below.

In some embodiments, the proximal hub 130 of the expandable framework 110 may be configured to releasably attach, join, couple, engage, or otherwise connect to the distal end of the delivery catheter 30. In some embodiments, the left atrial appendage closure device 100 and/or the expandable framework 110 may include an insert 140 disposed within the proximal hub 130. In some embodiments, the insert 140 may be configured to and/or adapted to releasably couple with, join to, mate with, or otherwise engage the distal end of the delivery catheter 30, as discussed herein. In the interest of clarity, not all features of the insert 140 described herein are shown in FIGS. 3-4. Some of these features may be shown in more detail in other figures.

In some embodiments, the insert 140 may include a collar 142 defining a circumferential wall 144 of the insert 140 configured to engage the proximal hub 130, a recess 146 extending axially into the insert 140 from a proximal end of the insert 140, and a post member 150 disposed within the recess 146 radially inward of the circumferential wall 144. The recess 146 may extend distally into the insert 140 from a proximal end of the insert 140 to a distal surface within the recess 146 defining a distal end of the recess 146. The post member 150 may be radially spaced apart from the collar 142 and/or the circumferential wall 144 to define an annular gap 148 (e.g., FIGS. 6-8) between the post member 150 and the collar 142 and/or the circumferential wall 144. The post member 150 may extend proximally from a distal end of the recess 146 and/or the distal surface within the recess 146 to a proximal surface 152 of the post member 150 disposed proximate the proximal end of the insert 140. In some embodiments, the proximal surface 152 of the post member 150 may be disposed distal of the proximal end of the insert 140. In some embodiments, the proximal surface 152 of the post member 150 may be disposed proximal of the proximal end of the insert 140. In some embodiments, the proximal surface 152 of the post member 150 may be disposed substantially flush with the proximal end of the insert 140.

As shown in FIG. 4, the insert 140 may extend distally into an interior of the left atrial appendage closure device 100 and/or the expandable framework 110. In some embodiments, the insert 140 may have a substantially cylindrical outer surface. In some embodiments, the insert 140 may be hollow and/or may include an interior space distal of the distal end of the recess 146 and/or the distal surface within the recess 146. An overall length of the insert 140 may vary depending on the construction of the insert 140 and/or components disposed within the interior space of the insert 140.

Figure 5:
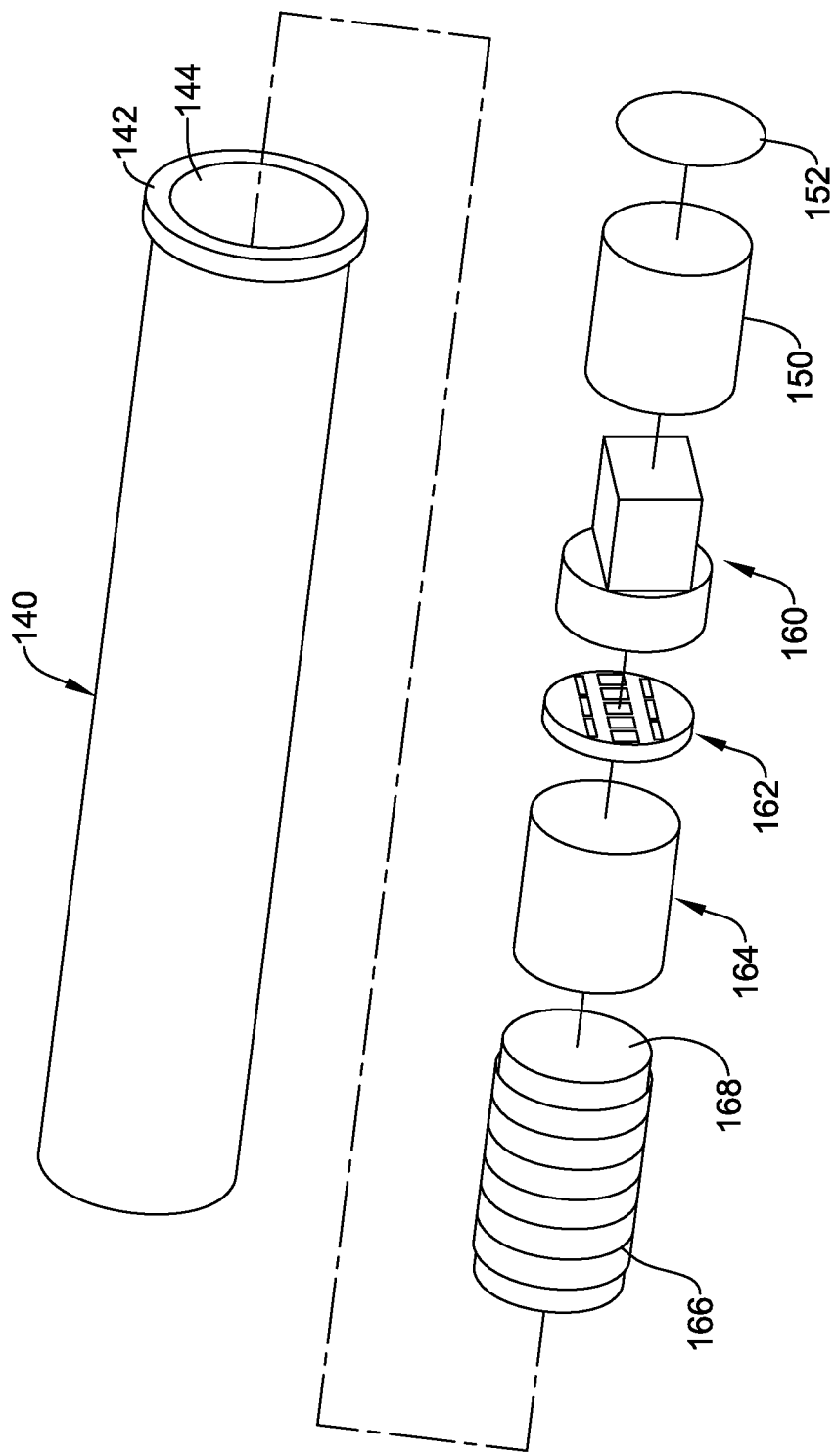
FIG. 5 is an exploded view illustrating aspects of an insert associated with the left atrial appendage closure device.

In one example configuration, as shown in FIG. 5, the insert 140 may include one or more internal components disposed within the interior space. In some embodiments, the insert may be devoid of any internal components. As such, any and/or all of the internal components may be considered optional in any particular example. The exploded view of FIG. 5 is one exemplary and non-limiting configuration of the insert 140. For example, the insert 140 may include a sensor 160 disposed within the insert 140 and/or the post member 150, the sensor 160 being in communication with the proximal surface 152 of the post member 150. In some embodiments, the sensor 160 may be a pressure sensor, the proximal surface 152 of the post member 150 may include a diaphragm extending across the proximal end of the post member 150, and a pressure transfer fluid may be disposed within the post member 150 between the sensor 160 and the proximal surface 152 (e.g., the diaphragm). The proximal surface 152 (e.g., the diaphragm) and/or the pressure transfer fluid may cooperate to sense and/or transmit a fluid pressure in a space proximal of the post member 150 (e.g., a left atrium) and/or adjacent the proximal surface 152 to the sensor 160 when the expandable framework 110 is disposed within an ostium of the left atrial appendage in the delivery configuration. In some embodiments, the sensor 160 may be configured to sense and/or detect temperature, flow rate, heart rate, electrical signals in the heart, heart rhythm, or other characteristics.

In some embodiments, the insert 140 may include an integrated circuit board 162 for controlling the sensor 160 and/or other internal components of the insert 140. In some embodiments, the insert 140 may include a communication coil 166 disposed within the interior space. In some embodiments, the communication coil 166 may be configured for bi-directional wireless communication and/or energy transfer. In some embodiments, the insert 140 may optionally include a battery 168. In some embodiments, the insert 140 may be powered "on-demand" via an inductive link. In some embodiments, the communication coil 166 may be and/or may form a part of the inductive link. In some embodiments, the insert 140 may include a capacitor 164 disposed within the interior space configured to act as a temporary power source for the sensor 160 and/or other internal components of the insert 140 (during "on-demand" energy transfer to the left atrial appendage closure device 100, for example). In some embodiments, the communication coil 166 may be wrapped around the battery 168, as shown in FIG. 5. In some embodiments, the communication coil 166 may be wrapped around the capacitor 164. In some embodiments, the communication coil 166 may be a stand-alone feature and/or may be wrapped around an inert and/or non-functional structure to maintain shape and/or form. Other configurations are also contemplated.

In some embodiments utilizing the battery 168, the battery 168 may be rechargeable. While a direct connection may be used to recharge the battery 168, such a configuration may be rather invasive to the patient. Accordingly, a wireless (e.g., inductive) recharging capability may be more desirable and far less invasive to the patient. In some embodiments, utilizing the battery 168, the battery 168 may not be rechargeable. When using a non-rechargeable battery 168, it is desirable to use a battery having a lifetime at least as long as the expected remaining lifetime of the patient to avoid needing to replace the battery 168 during a patient's later years when surgical procedures may be more challenging.

Figure 6:
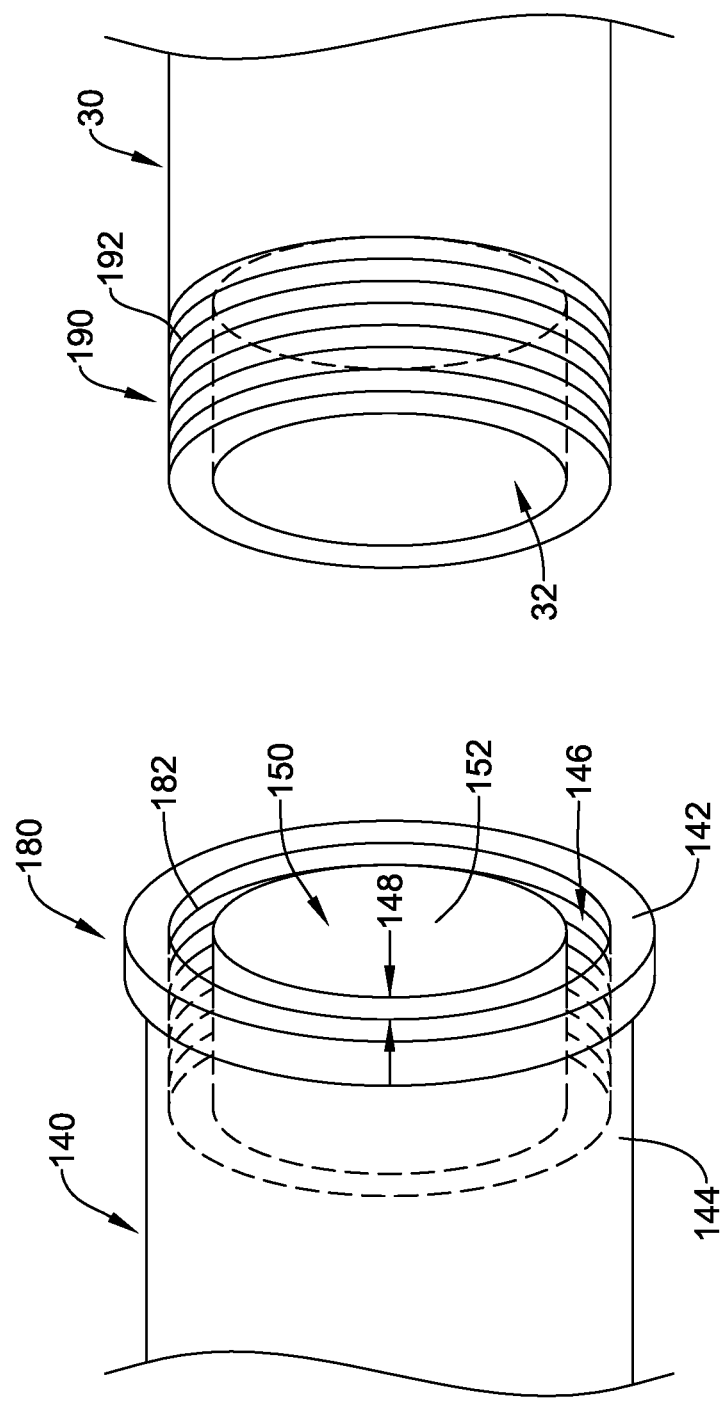
FIG. 6 illustrates aspects of a first connection structure and a second connection structure.

The insert 140 may include a first connection structure 180 disposed distal of the proximal surface 152. The delivery catheter 30 may include a second connection structure 190 proximate the distal end of the delivery catheter 30. The second connection structure 190 may be configured to engage the first connection structure 180 in the delivery configuration of the medical system 10. In some embodiments, the distal end of the delivery catheter 30 may include a hollow portion 32 configured to receive the post member 150 in the delivery configuration of the medical system 10, as shown in FIG. 6 for example. For the purpose of illustration, FIG. 6 shows aspects of the medical system 10 in a released configuration with the delivery catheter 30 disengaged from the left atrial appendage closure device 100.

In some embodiments, the first connection structure 180 may include a first threaded portion 182 disposed on an inside surface of the insert 140 (e.g., internal threads), as seen in FIG. 6. In the example of FIG. 6, the second connection structure 190 may include a second threaded portion 192 disposed proximate the distal end of the delivery catheter 30. The second threaded portion 192 may be disposed on an outside surface of the distal end of the delivery catheter 30 (e.g., external threads). The second threaded portion 192 may be configured to threadably mate with the first threaded portion 182 when the medical system 10 is in the delivery configuration (e.g., FIG. 10). In use, as the distal end of the delivery catheter 30 is inserted into the recess 146, the second connection structure 190 and/or the second threaded portion 192 may engage with and be rotated relative to the first connection structure 180 and/or the first threaded portion 182 to further engage the second threaded portion 192 with the first threaded portion 182 distal of the proximal surface 152 of the post member 150 such that the distal end of the delivery catheter 30 is translated axially and/or distally into the recess 146 of the insert 140. In the delivery configuration of the medical system 10, the first threaded portion 182 and the second threaded portion 192 may prevent relative axial movement between the left atrial appendage closure device 100 and the delivery catheter 30. The hollow portion 32 of the delivery catheter 30 may extend over and/or around the post member 150 such that the proximal surface 152 of the post member 150 may be protected from contact and/or damage during handling and/or implantation. In the delivery configuration of the medical system 10, the delivery catheter 30 may not contact the proximal surface 152 of the post member 150.

Figure 7:
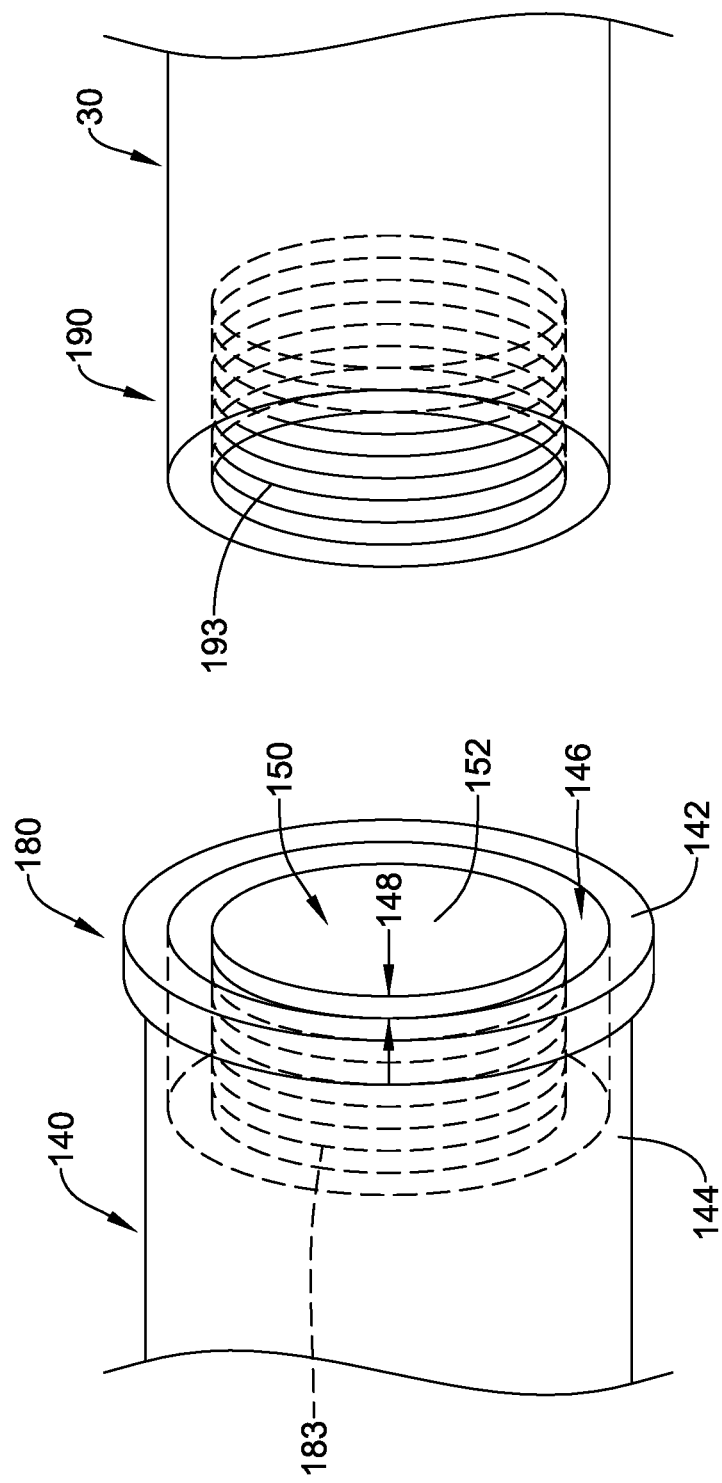
FIG. 7 illustrates aspects of a first connection structure and a second connection structure.

In some embodiments, the first connection structure 180 may include a first threaded portion 183 disposed on the outside surface of the post member 150 (e.g., external threads), as seen in FIG. 7. In the example of FIG. 7, the second connection structure 190 may include a second threaded portion 193 disposed proximate the distal end of the delivery catheter 30. The second threaded portion 193 may be disposed on an inside surface of the distal end of the delivery catheter 30 (e.g., internal threads). For example, the second threaded portion 193 may be disposed on an inside surface of the hollow portion 32. The second threaded portion 193 may be configured to threadably mate with the first threaded portion 183 when the medical system 10 is in the delivery configuration. In use, as the distal end of the delivery catheter 30 is inserted into the recess 146, the second connection structure 190 and/or the second threaded portion 193 may engage with and be rotated relative to the first connection structure 180 and/or the first threaded portion 183 to further engage the second threaded portion 193 with the first threaded portion 183 distal of the proximal surface 152 of the post member 150 such that the distal end of the delivery catheter 30 is translated axially and/or distally into the recess 146 of the insert 140. In the delivery configuration of the medical system 10, the first threaded portion 183 and the second threaded portion 193 may prevent relative axial movement between the left atrial appendage closure device 100 and the delivery catheter 30. The hollow portion 32 of the delivery catheter 30 may extend over and/or around the post member 150 such that the proximal surface 152 of the post member 150 may be protected from contact and/or damage during handling and/or implantation. In the delivery configuration of the medical system 10, the delivery catheter 30 may not contact the proximal surface 152 of the post member 150.

Figure 8:
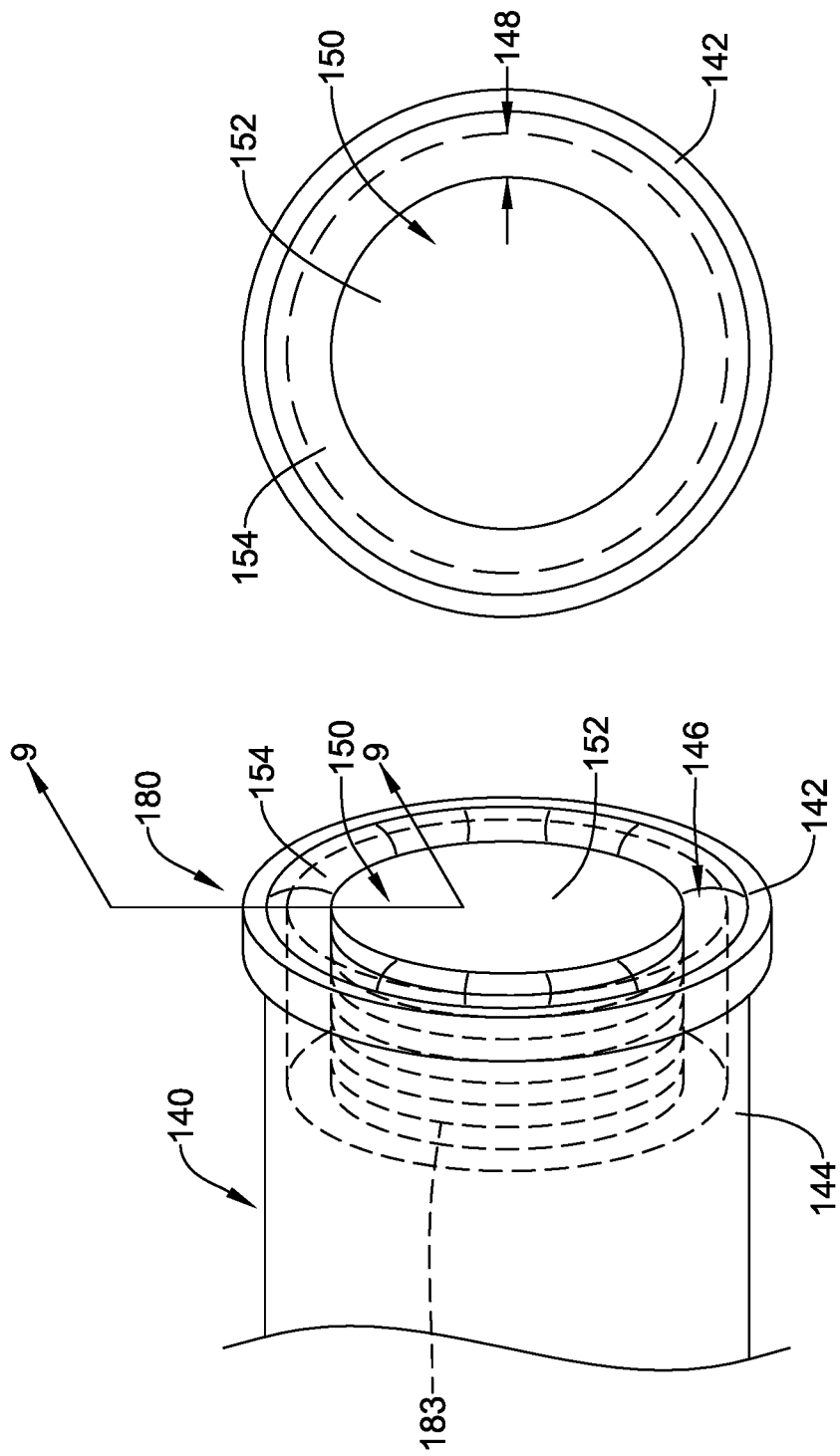
FIG. 8 illustrates aspects of the insert associated with the left atrial appendage closure device.
Figure 9:
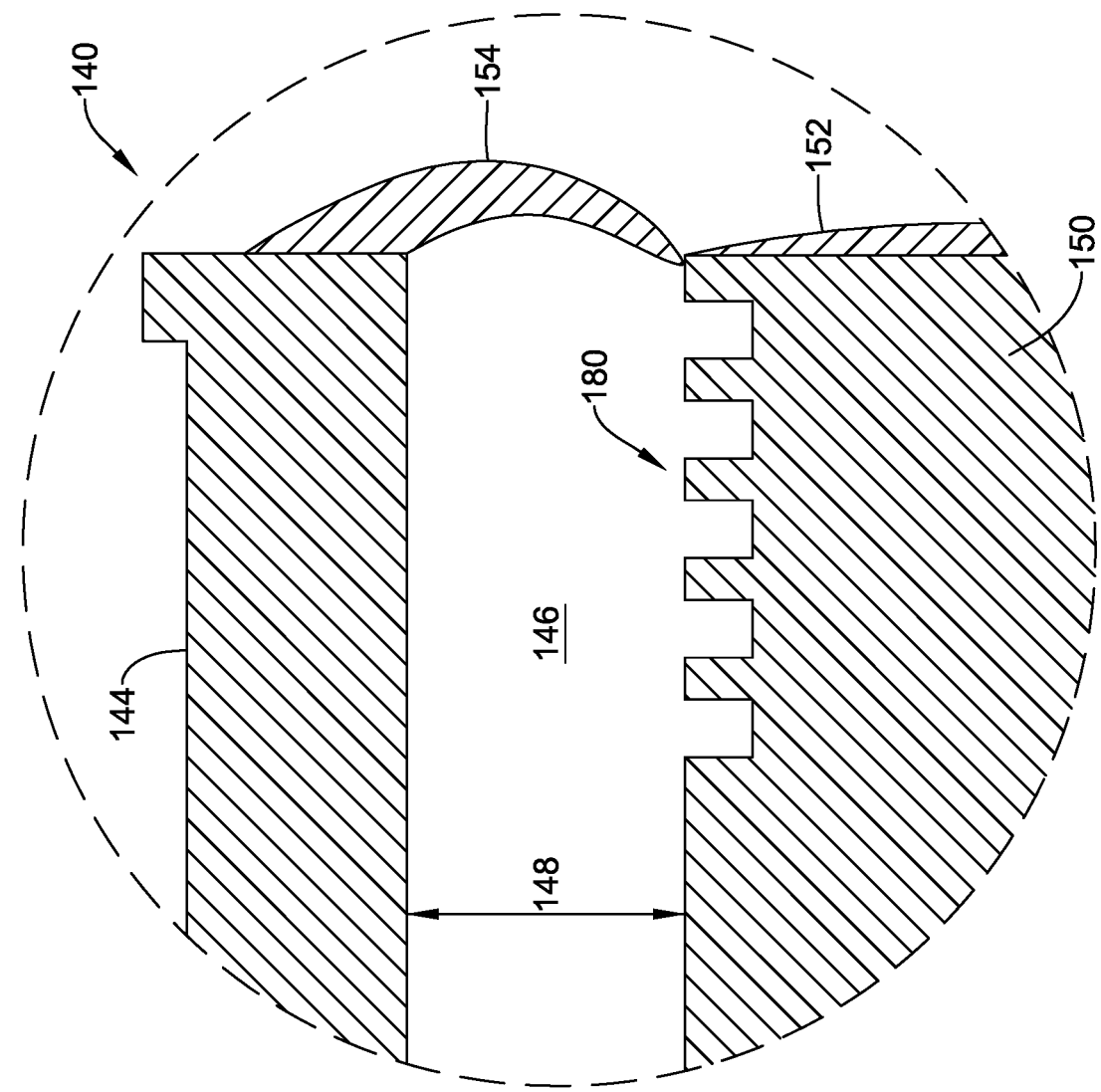
FIG. 9 is a partial cross-sectional view of FIG. 8 taken along the line 9-9.
Figure 10:
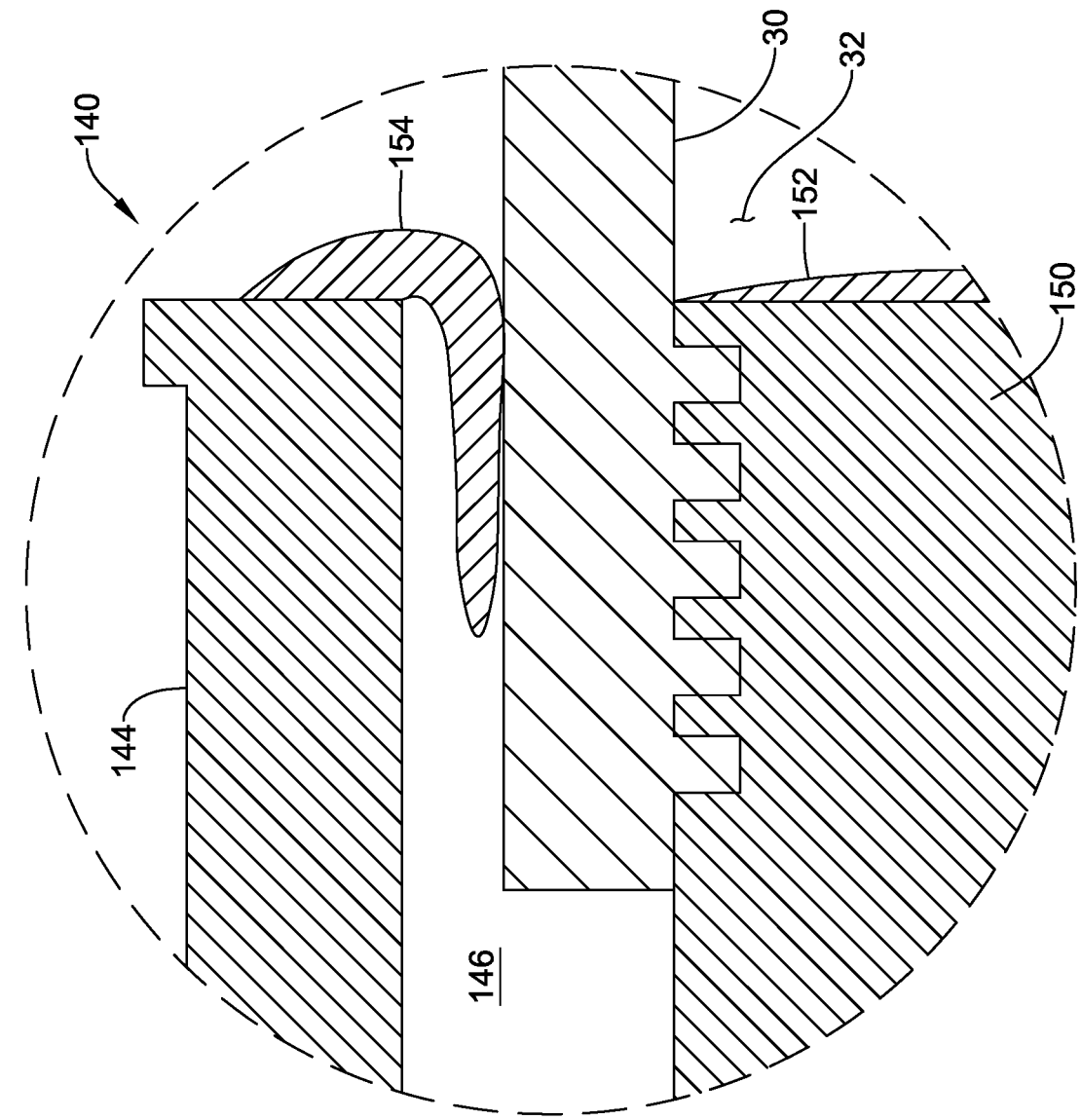
FIG. 10 illustrates aspects of the medical system in a delivery configuration and/or a deployed configuration.

FIGS. 8-10 illustrate selected aspects of medical system 10 and the insert 140 in more detail. As shown in FIG. 8 and as described herein, the insert 140 may include the collar 142 defining the circumferential wall 144 of the insert 140 configured to engage the proximal hub 130, the recess 146 extending axially into the insert 140 from the proximal end of the insert 140, and the post member 150 disposed within the recess 146 radially inward of the circumferential wall 144. The post member 150 may be radially spaced apart from the collar 142 and/or the circumferential wall 144 to define the annular gap 148 between the post member 150 and the collar 142 and/or the circumferential wall 144. For the purpose of illustration only, the insert 140 of FIGS. 8-10 is shown with aspects of the insert 140 in accordance with FIG. 7. However, any of the embodiments described herein may include and/or may be combined with aspects shown in FIGS. 8-10.

In at least some embodiments, the insert 140 may further include a gap seal 154 disposed in and/or extending across a proximal end of the annular gap 148 when the medical system 10 is disposed in the released configuration in which the delivery catheter 30 is disengaged from the left atrial appendage closure device 100 and/or the insert 140. In some embodiments, the gap seal 154 may be deflectable between a first position (e.g., FIG. 9) and a second position (e.g., FIG. 10). When the medical system 10 is in the released configuration, the gap seal 154 may be disposed in the first position. In the first position, the gap seal 154 may extend from the circumferential wall 144 to the post member 150. In the first position, the gap seal 154 may be in contact with both the circumferential wall 144 and the post member 150. In the first position, the gap seal 154 may be configured to seal off the annular gap 148 and/or the recess 146 from the circulatory system and/or the left atrium of the patient, thereby reducing the chance of developing thrombus therein. Additionally, in some embodiments, the gap seal 154 may include a coating or therapeutic agent configured to promote endothelization when exposed to the circulatory system and/or the left atrium of the patient.

When the medical system 10 is in the delivery configuration and/or the deployed configuration, the gap seal 154 may be disposed in the second position. In the second position, the gap seal 154 may be in contact with only one of the circumferential wall 144 and the post member 150. The gap seal 154 may be configured to deflect into the recess 146 to the second position by engagement with the distal end of the delivery catheter 30 and/or by engagement with the second connection structure 190 when the medical system 10 is in the delivery configuration. In the second position, the gap seal 154 may form a sealing engagement with an inner surface or an outer surface of the delivery catheter 30.

In some embodiments, the gap seal 154 may be fixedly attached to the circumferential wall 144 or the post member 150. The gap seal 154 may be configured to deflect radially away from the first connection structure 180, as shown in FIG. 10. While illustrated in FIG. 10 as being fixedly attached to the circumferential wall 144, it is contemplated that the gap seal 154 could be fixedly attached to the post member 150 (in the configuration of FIG. 6, for example). As shown in FIG. 10, in the delivery configuration of the medical system 10, the distal end of the delivery catheter 30 includes the hollow portion 32 configured to extend over the post member 150 and within the circumferential wall 144. For example, the hollow portion 32 may be disposable within the insert 140 radially inward of the circumferential wall 144 and radially outward of the post member 150 in the delivery configuration of the medical system 10. The distal end of the delivery catheter 30 may be disposed distal of the proximal end of the insert 140 and/or the proximal surface 152 of the post member 150. Some suitable, but non-limiting, examples of materials for the gap seal 154 are discussed below.

Figure 11:
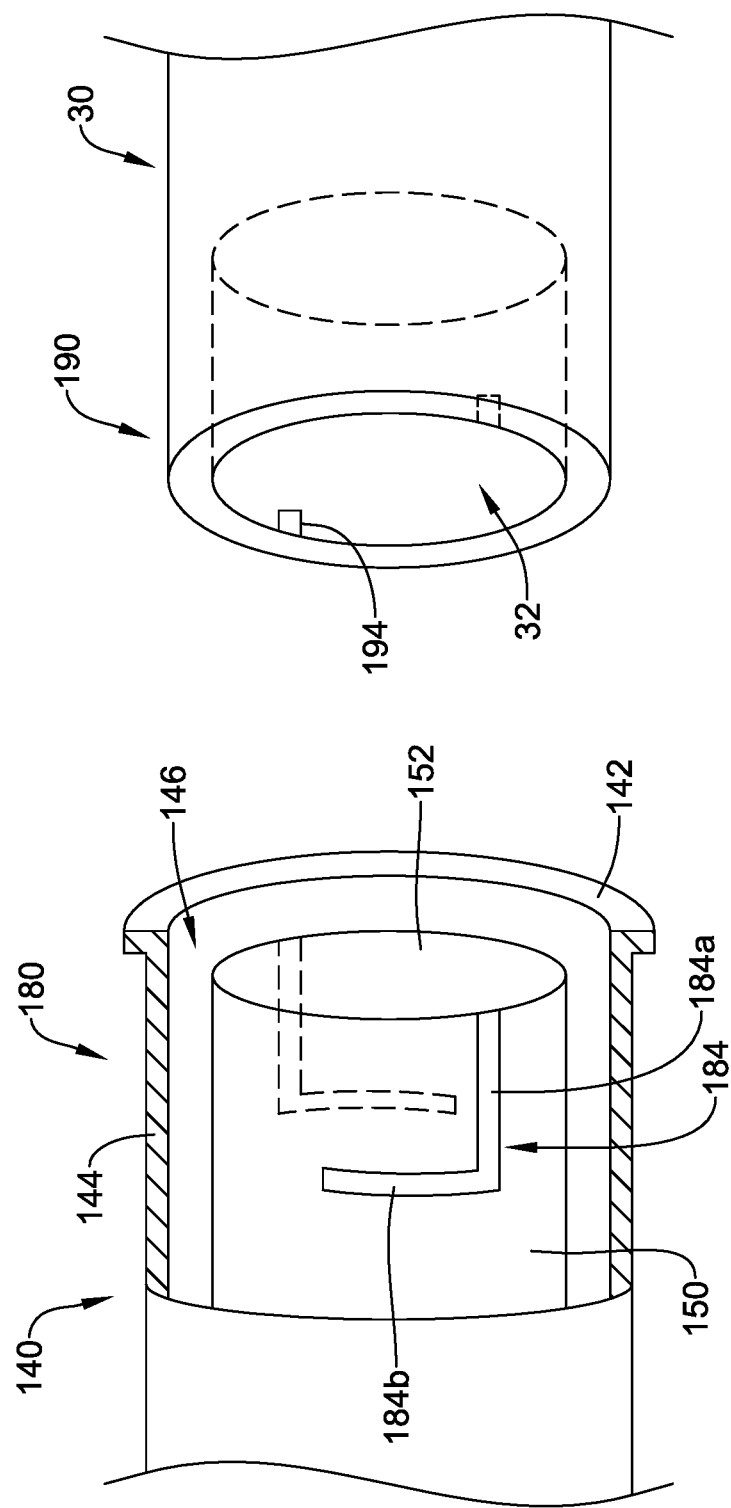
FIG. 11 illustrates aspects of a first connection structure and a second connection structure.
Figure 12:
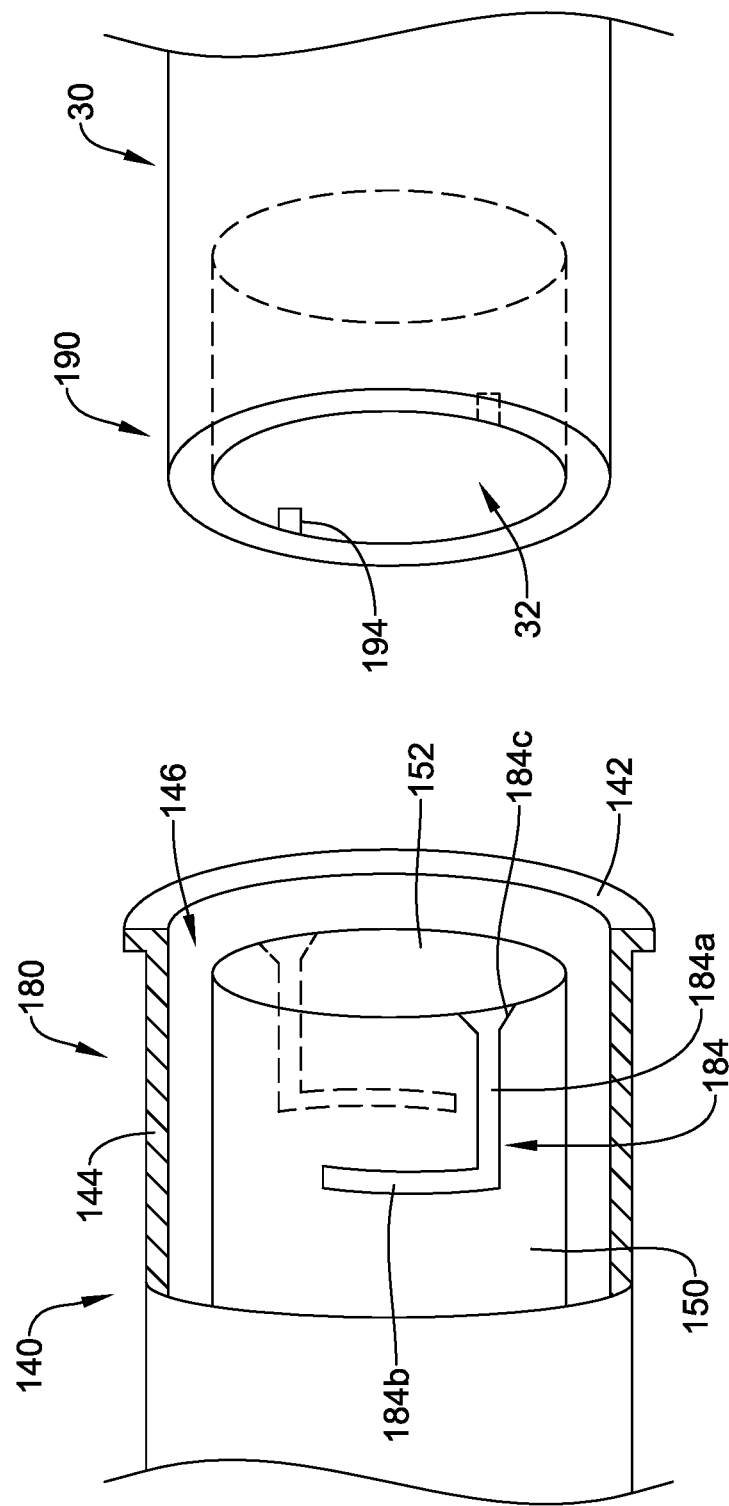
FIG. 12 illustrates aspects of a first connection structure and a second connection structure.

In some embodiments, the first connection structure 180 may include at least one groove 184 formed in the outside surface of the post member 150, as seen in FIG. 11. In some embodiments, the at least one groove 184 may include two grooves, three grooves, four grooves, or more grooves as needed or desired to achieve desired operational characteristics. The at least one groove 184 may each include a longitudinal portion 184A and a circumferential portion 184B extending from a distal end of the longitudinal portion 184A. In some embodiments, the longitudinal portion 184A of the at least one groove 184 may include a proximally widening taper 184C at a proximal end, as shown in FIG. 12. In the examples of FIGS. 11-12, the second connection structure 190 may include at least one radially extending projection 194 disposed proximate the distal end of the delivery catheter 30. In some embodiments, the second connection structure 190 may include at least one radially extending projection for each groove of the first connection structure 180, such that there is a corresponding and/or equal number of grooves and radially extending projections. The at least one radially extending projection 194 may be configured to engage the at least one groove 184 when the medical system 10 is in the delivery configuration. In use, as the distal end of the delivery catheter 30 is inserted into the recess 146, the second connection structure 190 and/or the at least one radially extending projection 194 may engage with the first connection structure 180 and/or the at least one groove 184 as the delivery catheter 30 is advanced distally. Upon reaching the distal end of the longitudinal portion 184A of the at least one groove 184, the delivery catheter 30 may be rotated relative to left atrial appendage closure device 100, the insert 140, and/or the post member 150 such that the at least one radially extending projection 194 is translated circumferentially within the circumferential portion 184B of the at least one groove 184 distal of the proximal surface 152 of the post member 150 to lock the delivery catheter 30 to the insert 140 and/or the left atrial appendage closure device 100 and prevent relative axial movement therebetween when the medical system 10 is in the delivery configuration. The hollow portion 32 of the delivery catheter 30 may extend over and/or around the post member 150 such that the proximal surface 152 of the post member 150 may be protected from contact and/or damage during handling and/or implantation. In the delivery configuration of the medical system 10, the delivery catheter 30 may not contact the proximal surface 152 of the post member 150.

Figure 13:
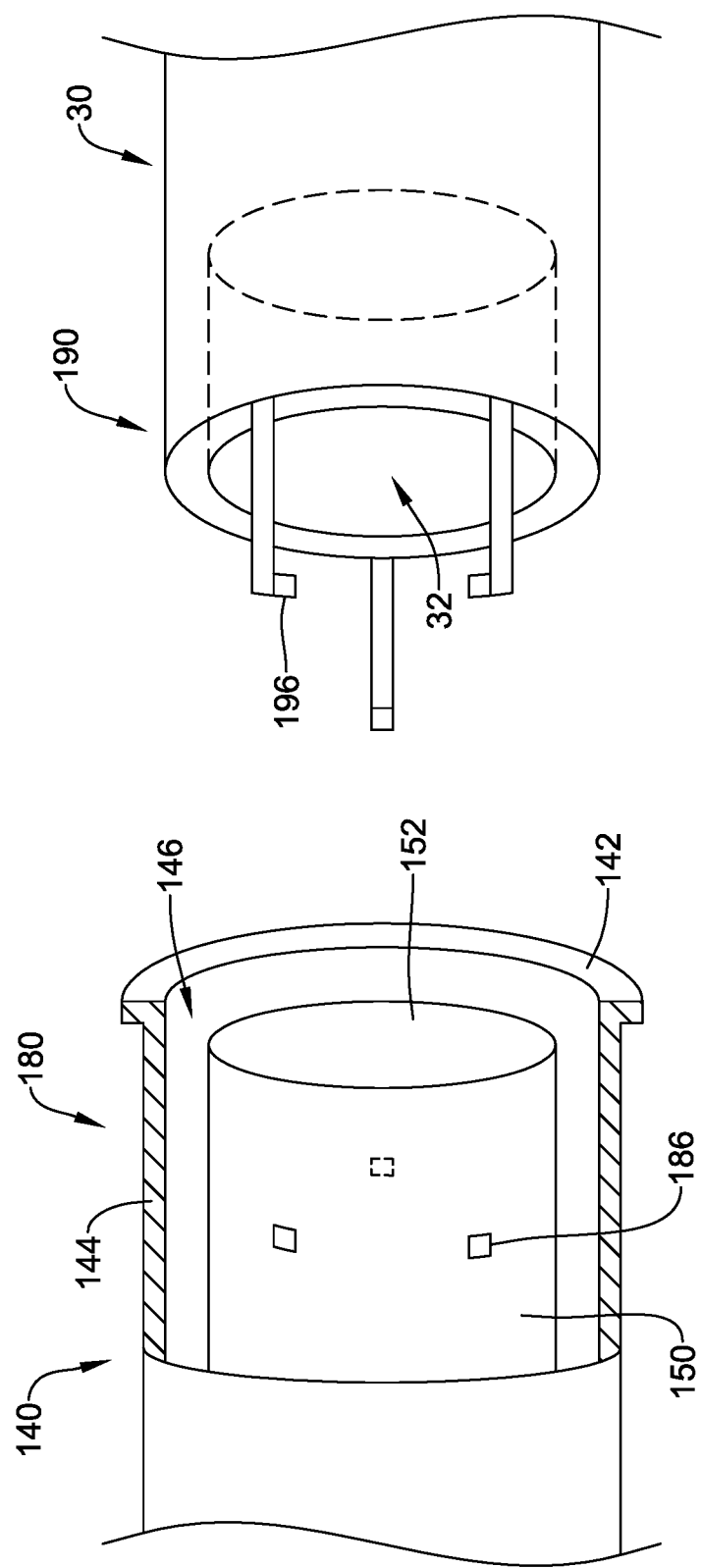
FIG. 13 illustrates aspects of a first connection structure and a second connection structure.

In some embodiments, the first connection structure 180 may include at least one detent 186 extending radially inward from the outside surface of the post member 150, as seen in FIG. 13. In some embodiments, the at least one detent 186 may include two detents, three detents, four detents, or more detents as needed or desired to achieve desired operational characteristics. In the example of FIG. 13, the second connection structure 190 may include at least one prong 196 disposed proximate the distal end of the delivery catheter 30. In some embodiments, the at least one prong 196 may extend distally from the distal end of the delivery catheter 30. The at least one prong 196 may be configured to engage the at least one detent 186 when the medical system 10 is in the delivery configuration. In some embodiments, the second connection structure 190 may include at least one prong for each detent of the first connection structure 180, such that there is a corresponding and/or equal number of prongs and detents. In use, as the distal end of the delivery catheter 30 is inserted into the recess 146, the second connection structure 190 and/or the at least one prong 196 may engage with the first connection structure 180 and/or the at least one detent 186. The at least one prong 196 may extend into the at least one detent 186 to lock the delivery catheter 30 to the insert 140 and/or the left atrial appendage closure device 100 and prevent relative axial movement therebetween when the medical system 10 is in the delivery configuration. In some embodiments, the hollow portion 32 of the delivery catheter 30 may extend over and/or around the post member 150 such that the proximal surface 152 of the post member 150 may be protected from contact and/or damage during handling and/or implantation. In the delivery configuration of the medical system 10, the delivery catheter 30 may not contact the proximal surface 152 of the post member 150.

Figure 14:
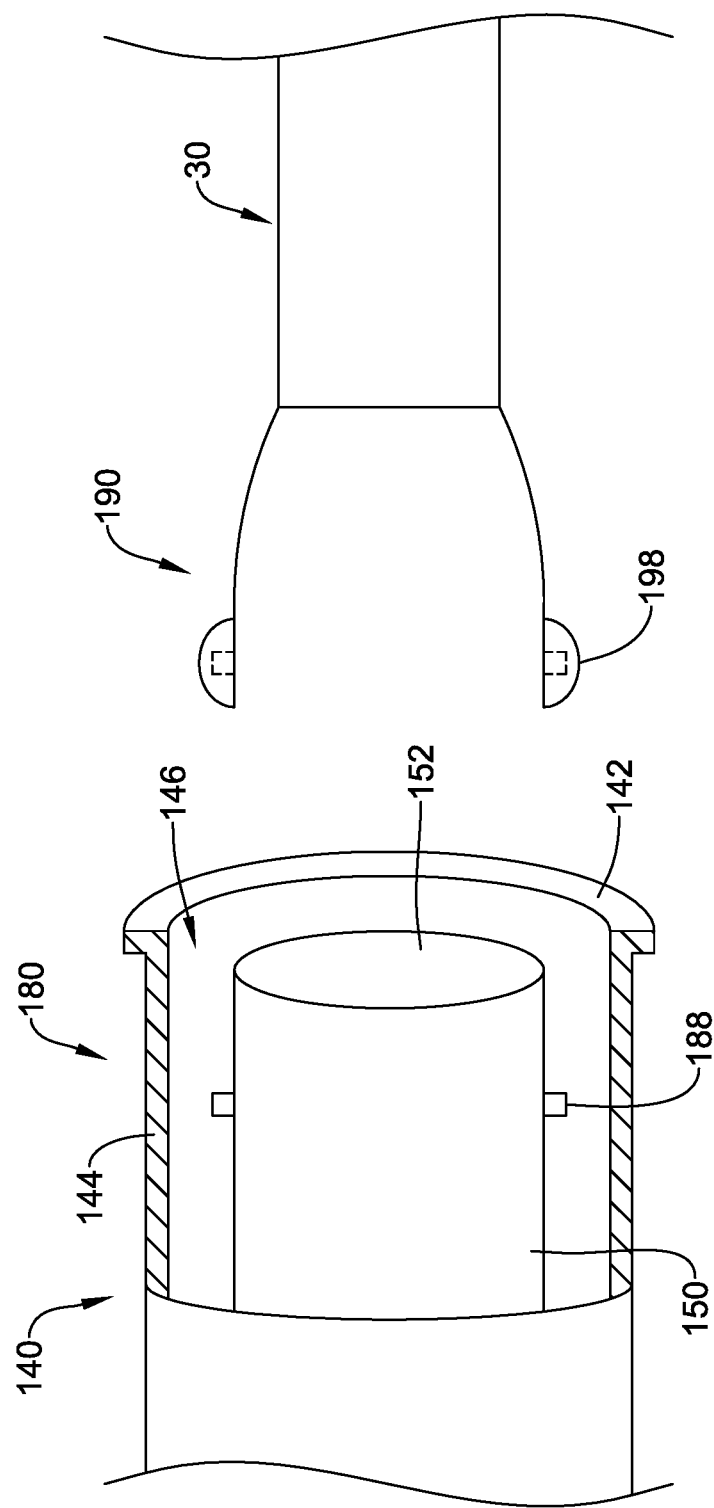
FIG. 14 illustrates aspects of a first connection structure and a second connection structure.

In some embodiments, the first connection structure 180 may include at least one projection 188 extending radially outward from the outside surface of the post member 150, as seen in FIG. 14. In some embodiments, the at least one projection 188 may include two projections, three projections, four projections, or more projections as needed or desired to achieve desired operational characteristics. In the example of FIG. 14, the second connection structure 190 may include two or more movable jaws 198 disposed proximate the distal end of the delivery catheter 30. In some embodiments, the two or more movable jaws 198 may extend distally from the distal end of the delivery catheter 30. The two or more movable jaws 198 may be configured to engage the at least one projection 188 when the medical system 10 is in the delivery configuration. In use, as the distal end of the delivery catheter 30 is inserted into the recess 146, the second connection structure 190 and/or the two or more movable jaws 198 may engage with the first connection structure 180 and/or the at least one projection 188. The two or more movable jaws 198 may be actuatable to clamp the post member 150 between the two or more movable jaws 198 distal of the proximal surface 152 of the post member 150 to lock the delivery catheter 30 to the insert 140 and/or the left atrial appendage closure device 100 and prevent relative axial movement therebetween when the medical system 10 is in the delivery configuration. In the delivery configuration of the medical system 10, the delivery catheter 30 may not contact the proximal surface 152 of the post member 150.

Figure 15:
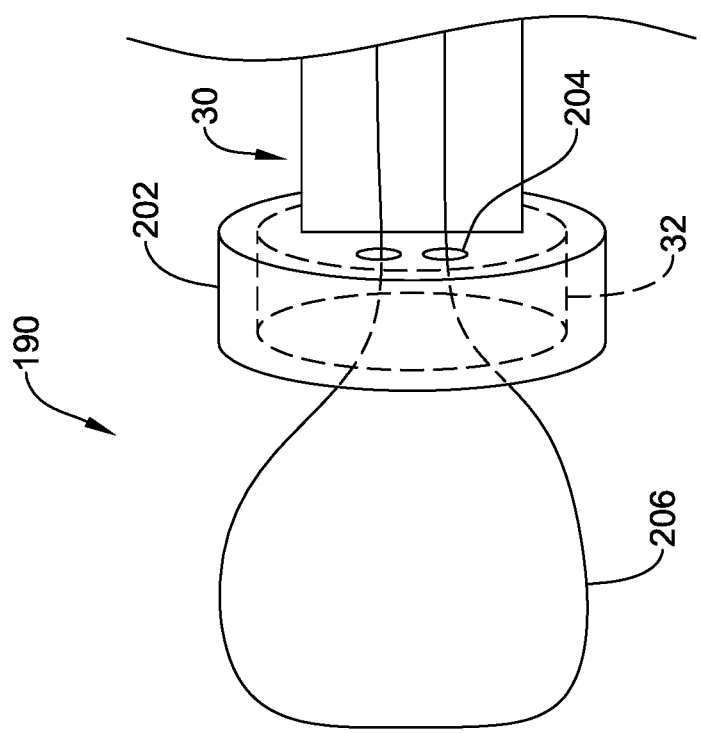
FIG. 15 illustrates aspects of a first connection structure and a second connection structure.
Figure 15:
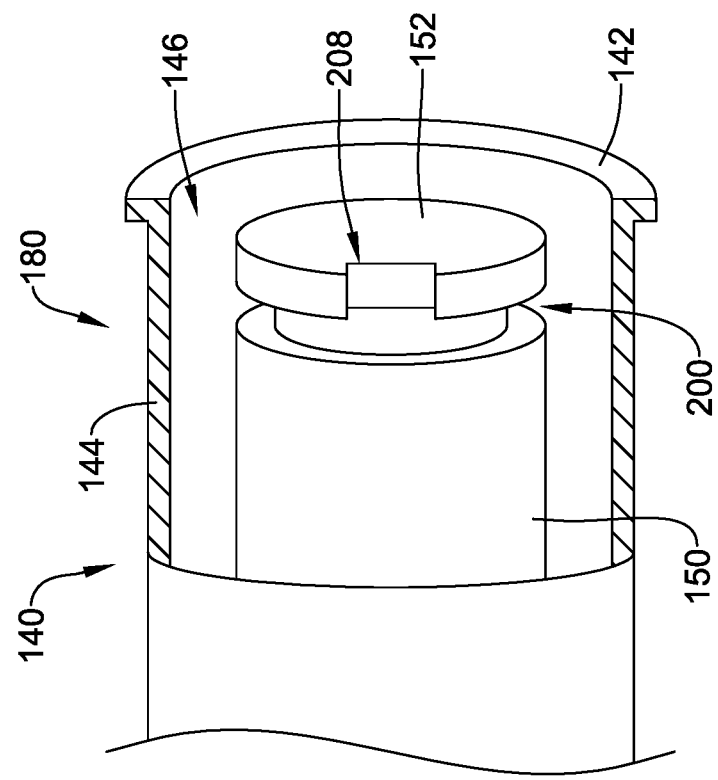

In some embodiments, the first connection structure 180 may include a channel 200 formed in and/or extending radially into the outside surface of the post member 150 and extending circumferentially around the post member 150 distal of the proximal surface 152, as seen in FIG. 15. The channel 200 may open radially outward from the central longitudinal axis of the insert 140 and/or the left atrial appendage closure device 100. In some embodiments, the channel 200 may be continuous or discontinuous around the post member 150 as needed or desired to achieve desired operational characteristics. The channel 200 may define a narrowed neck of the post member 150, wherein the proximal surface 152 is disposed on a head of the post member 150 proximal of the neck, the head having a greater outer diameter than the neck. In at least some embodiments, the head may include a notch 208 extending radially inward from an outer perimeter of the head to the narrowed neck.

In the example of FIG. 15, the second connection structure 190 may include a distal cap member 202 having the hollow portion 32 formed therein disposed proximate and/or at the distal end of the delivery catheter 30 and configured to span the proximal surface 152 of the post member 150. In some embodiments, the distal cap member 202 may include at least one aperture 204 formed in and/or through a laterally and/or radially extending surface of the distal cap member 202. The second connection structure 190 may further include a tether 206 extending longitudinally through the lumen 42 of the outer sheath 40 and/or alongside the delivery catheter 30, through the at least one aperture 204, and around the post member 150 in the delivery configuration of the medical system 10. In some embodiments, the tether 206 may extend into and/or through the hollow portion 32.

In use, the tether 206 may extend through the notch 208 and around the post member 150 in the channel 200 to secure the left atrial appendage closure device 100 to and/or against the distal cap member 202 of the delivery catheter 30 and prevent relative axial movement therebetween when the medical system 10 is in the delivery configuration. In some embodiments, the hollow portion 32 of the delivery catheter 30 and/or the distal cap member 202 may extend over and/or around the post member 150 such that the proximal surface 152 of the post member 150 may be protected from contact and/or damage during handling and/or implantation. In the delivery configuration of the medical system 10, the delivery catheter 30 may not contact the proximal surface 152 of the post member 150. Having the tether 206 extend through the notch 208 may permit a reduced tolerance and/or spacing between the hollow portion 32 and the head of the post member 150 in the delivery configuration.

Figure 16:
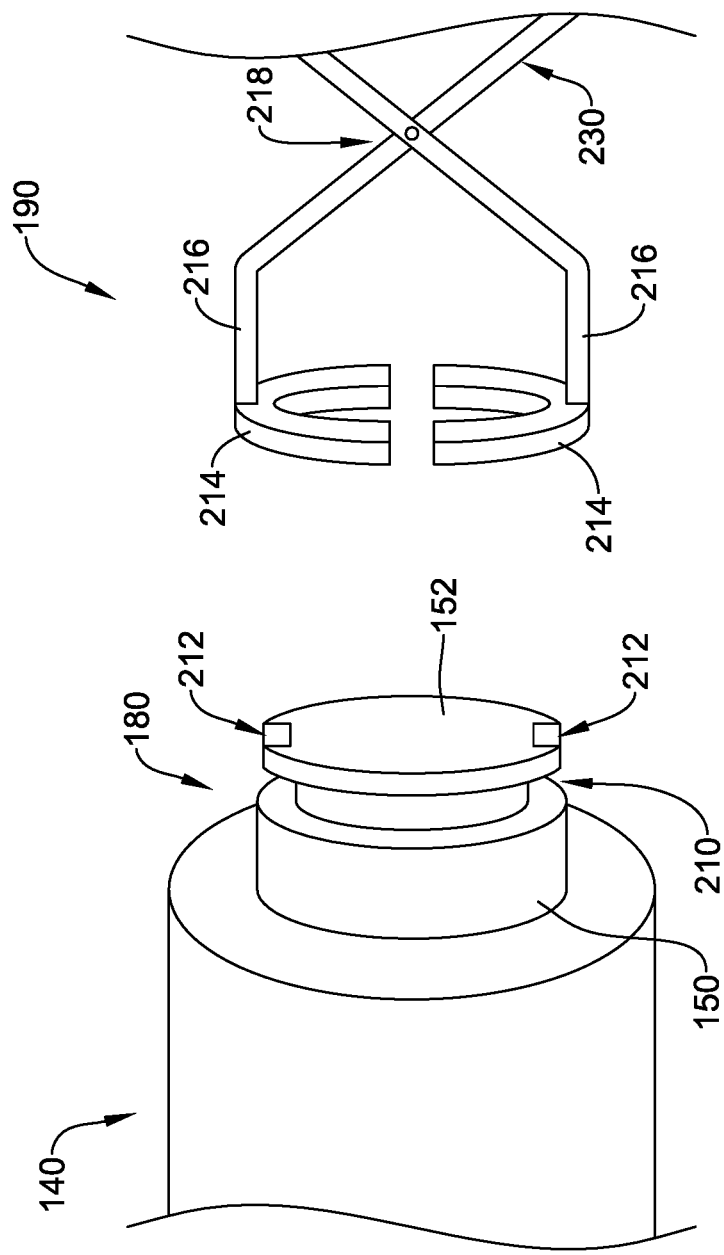
FIG. 16 illustrates aspects of a first connection structure and a second connection structure.

In some embodiments, the first connection structure 180 may include a channel 200 formed in and/or extending radially into the outside surface of the post member 150 and extending circumferentially around the post member 150 distal of the proximal surface 152, as seen in FIG. 16. The channel 210 may open radially outward from the central longitudinal axis of the insert 140 and/or the left atrial appendage closure device 100. In some embodiments, the channel 210 may be continuous or discontinuous around the post member 150 as needed or desired to achieve desired operational characteristics. The channel 210 may define a narrowed neck of the post member 150, wherein the proximal surface 152 is disposed on a head of the post member 150 proximal of the neck, the head having a greater outer diameter than the neck. In at least some embodiments, the head may include two notches 212 extending radially inward from an outer perimeter of the head to the narrowed neck.

In some embodiments, and as illustrated in FIG. 16, the insert 140 may be devoid of the collar 142 and/or the circumferential wall 144. For example, the post member 150 may extend proximally from the insert 140 without any surrounding feature(s). Other configurations are also contemplated, and the first connection structure 180 and the second connection structure 190 of FIG. 16 may be used in conjunction with the insert 140, the collar 142, and/or the circumferential wall 144 shown in other examples.

In the example of FIG. 16, the second connection structure 190 may include two movable jaws 216 disposed proximate the distal end of the delivery catheter 30. In some embodiments, the two movable jaws 216 may extend within and distally from the distal end of the delivery catheter 30. In some embodiments, the medical system 10 may be devoid of the delivery catheter 30 and the second connection structure 190 may be slidably disposed directly within the outer sheath 40. In some embodiments, the second connection structure 190 may include an elongate shaft portion 230 extending proximally from the two movable jaws 216 within the outer sheath 40. Each of the two movable jaws 216 may include an engagement element 214 extending radially inward from its jaw 216 that is curved, arced, and/or semi-circular in shape. In some embodiments, the two movable jaws 216 may be movably and/or pivotably joined together at a hinge point 218 proximal of the engagement element(s) 214, to permit relative movement of the engagement elements 214 in radially opposite directions. The elongate shaft portion 230 may extend proximally from the hinge point 218 and/or the hinge point 218 may distinguish the two movable jaws 216 from the elongate shaft portion 230.

The two movable jaws 216 and the engagement element(s) 214 may be configured to engage the channel 210 and the two notches 212 when the medical system 10 is in the delivery configuration. Each of the two notches 212 may correspond to and/or may be configured to engage one of the two movable jaws 216, and engagement of the two movable jaws 216 with the two notches 212 may prevent relative rotation between the first connection structure 180 and the second connection structure 190.

The two movable jaws 216 may be actuatable to clamp the post member 150 between the two movable jaws 216 distal of the proximal surface 152 of the post member 150 (e.g., within the channel 210) to lock the elongate shaft 230 to the insert 140 and/or the left atrial appendage closure device 100 and prevent relative axial movement therebetween when the medical system 10 is in the delivery configuration. In the delivery configuration of the medical system 10, the elongate shaft 230, the two movable jaws 216, and/or the engagement element(s) 214 may not contact the proximal surface 152 of the post member 150.

Other means of releasably coupling and/or engaging the expandable framework 110 to the distal end of the delivery catheter 30 are also contemplated.

Figure 17:
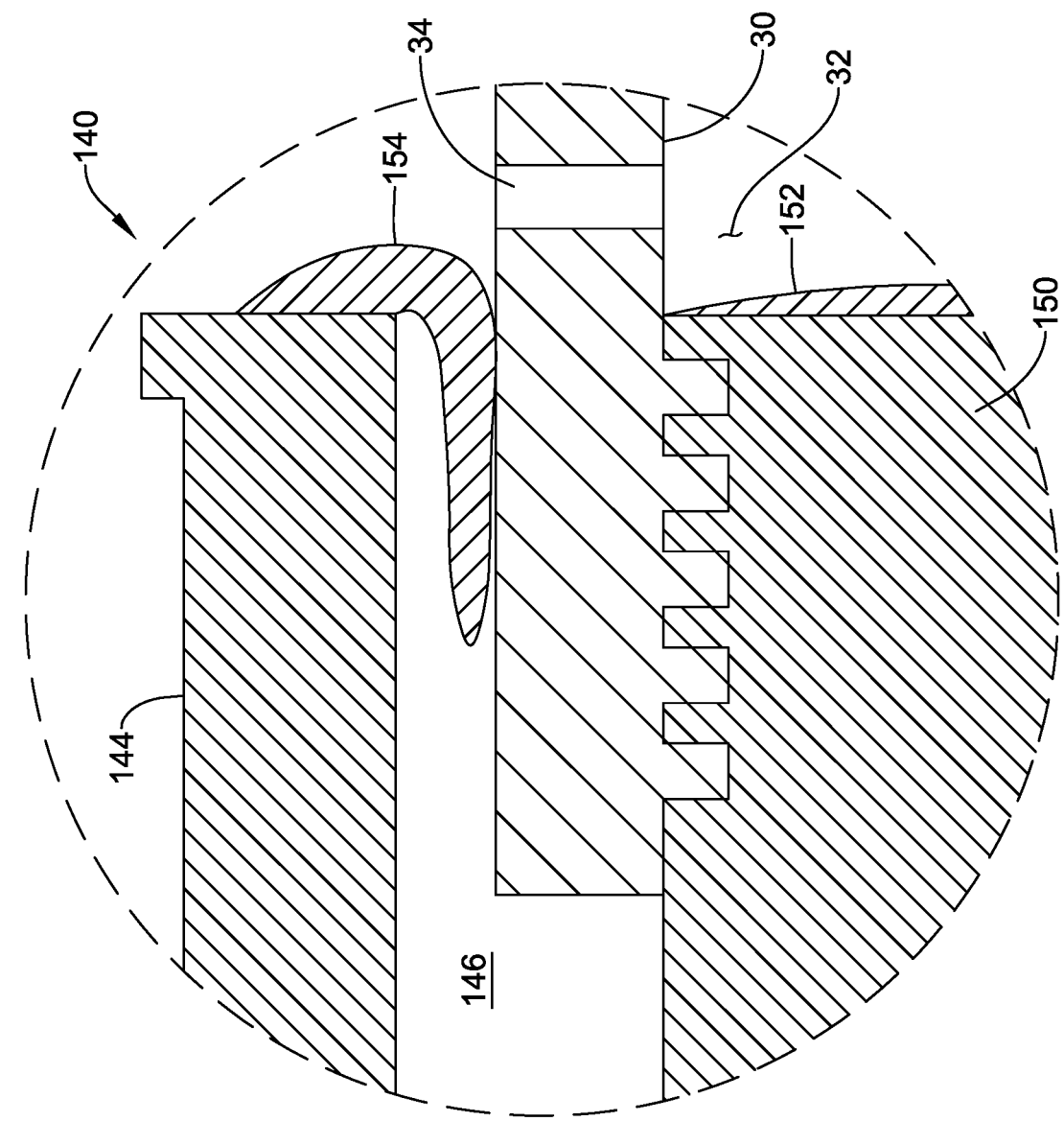
FIG. 17 illustrates aspects of the medical system in the delivery configuration and/or the deployed configuration.

In addition or alternatively to any configuration described herein, the delivery catheter 30 may include at least one aperture 34 extending through a side wall of the delivery catheter 30 into the hollow portion 32 proximate the distal end of the delivery catheter 30, as shown in FIG. 17. In the delivery configuration, the at least one aperture 34 may be disposed proximal of the insert 140 and/or the proximal surface 152 of the post member 150. The at least one aperture 34 may permit fluid communication between an exterior of the delivery catheter 30 and the proximal surface 152 of the post member 150 when the medical system 10 is in the delivery configuration. This may be useful when the practitioner wants to detect and/or measure left atrial pressure and/or other characteristics with the sensor 160 prior to releasing the left atrial appendage closure device 100.

The materials that can be used for the various components of the medical system 10 and/or the left atrial appendage closure device 100 and the various elements thereof disclosed herein may include those commonly associated with medical devices. For simplicity purposes, the following discussion refers to the medical system 10 and/or the left atrial appendage closure device 100. However, this is not intended to limit the devices and methods described herein, as the discussion may be applied to other elements, members, components, or devices disclosed herein, such as, but not limited to, the delivery catheter 30, the outer sheath 40, the expandable framework 110, the plurality of anchor members 112, the occlusive element 120, the insert 140, and/or elements or components thereof.

In some embodiments, the medical system 10 and/or the left atrial appendage closure device 100, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical system 10 and/or the left atrial appendage closure device 100, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical system 10 and/or the left atrial appendage closure device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical system 10 and/or the left atrial appendage closure device 100 to achieve the same result.

In some embodiments, a degree of Magnetic Resonance Imaging (MRI) compatibility is imparted into the medical system 10 and/or the left atrial appendage closure device 100 and/or other elements disclosed herein. For example, the medical system 10 and/or the left atrial appendage closure device 100, and/or components or portions thereof, may be made of a material that does not substantially distort the image and create substantial artifacts (i.e., gaps in the image). Certain ferromagnetic materials, for example, may not be suitable because they may create artifacts in an MRI image. The medical system 10 and/or the left atrial appendage closure device 100, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the medical system 10 and/or the left atrial appendage closure device 100 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical system 10 and/or the left atrial appendage closure device 100 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical system 10 and/or the left atrial appendage closure device 100 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical system, comprising:
a left atrial appendage closure device including an expandable framework and a proximal hub centered on a central longitudinal axis of the expandable framework;
wherein an insert is disposed within the proximal hub, the insert including a circumferential wall and a collar configured to engage the proximal hub, a recess extending into the insert from a proximal end of the insert, and a post member disposed within the recess;
wherein the post member is radially spaced apart from the circumferential wall to define a gap between the post member and the circumferential wall, and the post member extends proximally from a distal end of the recess to a proximal surface of the post member;
wherein the insert includes a first connection structure disposed within the recess; and
a delivery catheter having a second connection structure proximate a distal end of the delivery catheter, the second connection structure being configured to engage the first connection structure in a delivery configuration of the medical system;
wherein the insert includes a gap seal extending radially across the gap and covering a proximal end of the gap when the medical system is disposed in a released configuration in which the delivery catheter is disengaged from the left atrial appendage closure device;
wherein the distal end of the delivery catheter includes a hollow portion configured to receive the post member in the delivery configuration;
wherein the gap seal is fixedly attached to only one of the circumferential wall or the post member and extends across the proximal end of the gap to engage the other of the circumferential wall or the post member when the medical system is disposed in the released configuration.

2. The medical system of claim 1, wherein a sensor is disposed within the post member.

3. The medical system of claim 2, wherein the sensor is a pressure sensor and the proximal surface is a diaphragm extending across a proximal end of the post member, the diaphragm being configured to transmit a pressure within a left atrium to the pressure sensor when the expandable framework is disposed within an ostium of the left atrial appendage.

4. The medical system of claim 3, wherein the delivery catheter includes at least one aperture extending through a side wall of the delivery catheter proximate the distal end of the delivery catheter.

5. The medical system of claim 1, wherein the gap seal is configured to deflect into the recess when the medical system is in the delivery configuration.

6. The medical system of claim 1, wherein the first connection structure includes a first threaded portion disposed on an outside surface of the post member or an inside surface of the collar.

7. The medical system of claim 6, wherein the second connection structure includes a second threaded portion disposed proximate the distal end of the delivery catheter, the second threaded portion being configured to threadably mate with the first threaded portion when the medical system is in the delivery configuration.

8. The medical system of claim 1, wherein the first connection structure includes at least one groove formed in an outside surface of the post member or an inside surface of the collar, wherein the at least one groove includes a longitudinal portion and a circumferential portion extending from a distal end of the longitudinal portion.

9. The medical system of claim 8, wherein the second connection structure includes at least one radially extending projection proximate the distal end of the delivery catheter, the at least one radially extending projection being configured to engage the at least one groove when the medical system is in the delivery configuration.

10. The medical system of claim 1, wherein the first connection structure includes at least one projection extending radially outward from the post member.

11. The medical system of claim 10, wherein the second connection structure includes two or more movable jaws configured to engage the at least one projection to clamp the post member between the two or more movable jaws when the medical system is in the delivery configuration.

12. The medical system of claim 1, wherein the first connection structure includes a channel formed in an outside surface of the post member and extending circumferentially around the post member distal of the proximal surface.

13. The medical system of claim 12, wherein the second connection structure includes:
a distal cap member disposed at the distal end of the delivery catheter and configured to span the proximal surface of the post member, wherein the distal cap member includes at least one aperture formed in a laterally extending surface of the distal cap member; and
a tether extending longitudinally alongside the delivery catheter, through the at least one aperture, and around the post member within the channel when the medical system is in the delivery configuration.

14. A medical system, comprising:
a left atrial appendage closure device including an expandable framework and a proximal hub centered on a central longitudinal axis of the expandable framework;
wherein an insert is disposed within the proximal hub, the insert including a collar defining a circumferential wall of the insert configured to engage the proximal hub, a recess extending axially into the insert from a proximal end of the insert, and a post member disposed within the recess;
wherein the post member is radially spaced apart from the circumferential wall to define an annular gap between the post member and the circumferential wall, and the post member extends proximally from a distal end of the recess to a proximal surface of the post member;
wherein the insert includes a first connection structure disposed within the recess distal of the proximal surface of the post member;
wherein a pressure sensor is disposed within the post member and in communication with the proximal surface of the post member for sensing a fluid pressure proximal of the left atrial appendage closure device; and
a delivery catheter having a second connection structure proximate a distal end of the delivery catheter, the second connection structure being configured to engage the first connection structure in a delivery configuration of the medical system;
wherein the insert includes a gap seal extending radially across the annular gap and covering a proximal end of the annular gap when the medical system is disposed in a released configuration in which the delivery catheter is disengaged from the left atrial appendage closure device;
wherein the distal end of the delivery catheter includes a hollow portion configured to extend over the post member and within the circumferential wall in the delivery configuration such that the distal end of the delivery catheter is disposed distal of the proximal end of the insert;
wherein the gap seal is fixedly attached to only one of the circumferential wall or the post member and extends across the proximal end of the annular gap to engage the other of the circumferential wall or the post member when the medical system is disposed in the released configuration.

15. A medical system, comprising:
a left atrial appendage closure device including a self-expanding framework and a proximal hub centered on a central longitudinal axis of the expandable framework;
wherein an insert is disposed within the proximal hub, the insert including a collar defining a circumferential wall of the insert configured to engage the proximal hub, a recess extending axially into the insert from a proximal end of the insert, and a post member disposed within the recess and spaced apart radially inward from the circumferential wall by a gap;
wherein the post member extends proximally from a distal end of the recess to a proximal surface of the post member;
wherein a sensor, a capacitor, and a communication coil are disposed within the insert; and
a delivery catheter including a hollow portion disposable within the insert radially inward of the circumferential wall and radially outward of the post member in a delivery configuration of the medical system;
wherein the insert includes a gap seal extending radially across the gap and covering a proximal end of the gap when the medical system is disposed in a released configuration in which the delivery catheter is disengaged from the left atrial appendage closure device;
wherein the gap seal is fixedly attached to only one of the circumferential wall or the post member and extends across the proximal end of the gap to engage the other of the circumferential wall or the post member when the medical system is disposed in the released configuration.

16. The medical system of claim 15, wherein the insert includes a first connection structure disposed distal of the proximal surface of the post member and the delivery catheter includes a second connection structure configured to engage the first connection structure in the delivery configuration of the medical system.

17. The medical system of claim 15, wherein in the delivery configuration of the medical system, the delivery catheter does not contact the proximal surface of the post member.

18. The medical system of claim 15, wherein the left atrial appendage closure device includes an occlusive element disposed over at least a portion of the expandable framework;
wherein the expandable framework is configured to shift between a collapsed configuration and a deployed configuration;
wherein the occlusive element is configured to prevent thrombi from exiting a left atrial appendage when the expandable framework is disposed within an ostium of the left atrial appendage in the deployed configuration.

19. The medical system of claim 18, wherein the expandable framework includes a plurality of interconnected struts joined together at the proximal hub.

* * * * *